(12) United States Patent
McGuckin, Jr. et al.

(10) Patent No.: US 6,749,622 B2
(45) Date of Patent: Jun. 15, 2004

(54) VASCULAR CLOSURE

(75) Inventors: James F. McGuckin, Jr., Radnor, PA (US); Christopher W. Maurer, Malden, MA (US); Walter H. Peters, Downington, PA (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

(21) Appl. No.: 10/269,899

(22) Filed: Oct. 11, 2002

(65) Prior Publication Data
US 2003/0093096 A1 May 15, 2003

Related U.S. Application Data

(63) Continuation of application No. 09/659,648, filed on Sep. 12, 2000.
(60) Provisional application No. 60/153,736, filed on Sep. 13, 1999.

(51) Int. Cl.[7] .................................. A61B 17/08
(52) U.S. Cl. .................... 606/213; 606/151; 606/153; 606/215
(58) Field of Search ................ 606/151–158, 606/213, 215, 216, 219

(56) References Cited

U.S. PATENT DOCUMENTS

| | | |
|---|---|---|
| 3,874,388 A | 4/1975 | King et al. |
| 3,958,576 A | 5/1976 | Komiya |
| 4,007,743 A | 2/1977 | Blake |
| 4,031,569 A | 6/1977 | Jacob |
| 4,317,445 A | 3/1982 | Robinson |
| 4,485,816 A | 12/1984 | Krumme |
| 4,505,274 A | 3/1985 | Speelman |
| 4,512,338 A | 4/1985 | Balko et al. |
| 4,610,671 A | 9/1986 | Luther |

(List continued on next page.)

FOREIGN PATENT DOCUMENTS

| | | |
|---|---|---|
| DE | 19604817 | 8/1997 |
| EP | 0637431 | 2/1995 |
| EP | 0920842 | 6/1999 |
| WO | 9707741 | 3/1997 |
| WO | 9827868 | 7/1998 |
| WO | 9900055 | 1/1999 |
| WO | 9905977 | 2/1999 |
| WO | 9938454 | 8/1999 |

Primary Examiner—Michael J. Milano
Assistant Examiner—D. Jacob Davis
(74) Attorney, Agent, or Firm—Neil D. Gershon

(57) ABSTRACT

Clip apparatus for closing a vessel aperture resulting from insertion of a surgical implement comprising an elongated strand comprising a central portion and extremity portions extending from said central portion. The tips of said extremity portions remote from said central portion are shaped to retain tissue encountered thereby. The extremity portions have memory characteristics seeking to cause said extremity portions to curl with respect to said central portions to retain tissue engaged thereby when said strand is in an unconstrained disposition.

13 Claims, 28 Drawing Sheets

U.S. PATENT DOCUMENTS

| | | | |
|---|---|---|---|
| 4,665,906 A | 5/1987 | Jervis | |
| 4,676,245 A | 6/1987 | Fukuda | |
| 4,744,364 A | 5/1988 | Kensey | |
| 4,917,089 A | 4/1990 | Sideris | |
| 4,924,866 A | 5/1990 | Yoon | |
| 4,971,068 A | 11/1990 | Sahi | |
| 5,021,059 A | 6/1991 | Kensey et al. | |
| 5,047,047 A | 9/1991 | Yoon | |
| 5,061,274 A | 10/1991 | Kensey | |
| 5,108,420 A | 4/1992 | Marks | |
| 5,171,252 A | 12/1992 | Friedland | |
| 5,192,300 A | 3/1993 | Fowler | |
| 5,192,301 A | 3/1993 | Kamiya et al. | |
| 5,192,302 A | 3/1993 | Kensey et al. | |
| 5,222,974 A | 6/1993 | Kensey et al. | |
| 5,279,572 A | 1/1994 | Hokama | |
| 5,282,827 A | 2/1994 | Kensey et al. | |
| 5,306,254 A | 4/1994 | Nash et al. | |
| 5,312,435 A | 5/1994 | Nash et al. | |
| 5,385,554 A | 1/1995 | Brimhall | |
| RE34,866 E | 2/1995 | Kensey et al. | |
| 5,411,520 A | 5/1995 | Nash et al. | |
| 5,443,481 A | 8/1995 | Lee | |
| 5,451,235 A | 9/1995 | Lock et al. | |
| 5,474,557 A | 12/1995 | Mai | |
| 5,478,352 A | 12/1995 | Fowler | |
| 5,478,353 A | 12/1995 | Yoon | |
| 5,486,195 A | 1/1996 | Myers et al. | |
| 5,531,759 A | 7/1996 | Kensey et al. | |
| 5,540,716 A * | 7/1996 | Hlavacek | 606/219 |
| 5,545,178 A | 8/1996 | Kensey et al. | |
| 5,549,633 A | 8/1996 | Evans et al. | |
| 5,591,204 A | 1/1997 | Janzen et al. | |
| 5,593,422 A | 1/1997 | Muijs Van de Moer et al. | |
| 5,620,461 A | 4/1997 | Muijs Van De Moer et al. | |
| 5,630,833 A | 5/1997 | Katsaros et al. | |
| 5,643,317 A | 7/1997 | Pavcnik et al. | |
| 5,649,959 A | 7/1997 | Hannam et al. | |
| 5,662,681 A | 9/1997 | Nash et al. | |
| 5,674,231 A | 10/1997 | Green et al. | |
| 5,676,689 A | 10/1997 | Kensey et al. | |
| 5,690,674 A | 11/1997 | Diaz | |
| 5,700,277 A | 12/1997 | Nash et al. | |
| 5,702,421 A | 12/1997 | Schneidt | |
| 5,709,707 A | 1/1998 | Lock et al. | |
| 5,725,498 A | 3/1998 | Janzen et al. | |
| 5,728,132 A | 3/1998 | Van Tassel et al. | |
| 5,728,133 A | 3/1998 | Kontos | |
| 5,741,297 A | 4/1998 | Simon | |
| 5,782,860 A | 7/1998 | Epstein et al. | |
| 5,782,861 A | 7/1998 | Cragg et al. | |
| 5,810,846 A | 9/1998 | Virnich et al. | |
| 5,810,884 A | 9/1998 | Kim | |
| 5,820,628 A | 10/1998 | Middleman et al. | |
| 5,861,003 A | 1/1999 | Latson et al. | |
| 5,893,856 A * | 4/1999 | Jacob et al. | 606/151 |
| 5,910,155 A | 6/1999 | Ratcliff et al. | |
| 5,916,236 A | 6/1999 | Muijs Van de Moer et al. | |
| 5,919,207 A | 7/1999 | Taheri | |
| 5,964,782 A | 10/1999 | Lafontaine et al. | |
| 5,976,159 A | 11/1999 | Bolduc et al. | |
| 5,976,174 A | 11/1999 | Ruiz | |
| 5,984,949 A | 11/1999 | Levin | |
| 6,001,110 A | 12/1999 | Adams | |
| 6,007,563 A | 12/1999 | Nash et al. | |
| 6,015,417 A | 1/2000 | Reynolds, Jr. | |
| 6,033,427 A | 3/2000 | Lee | |
| 6,048,357 A | 4/2000 | Kontos | |
| 6,056,768 A | 5/2000 | Cates et al. | |
| 6,063,085 A | 5/2000 | Tay et al. | |
| 6,071,300 A | 6/2000 | Brenneman et al. | |
| 6,077,281 A | 6/2000 | Das | |
| 6,080,182 A | 6/2000 | Shaw et al. | |
| 6,080,183 A | 6/2000 | Tsugita et al. | |
| 6,113,611 A | 9/2000 | Allen et al. | |
| 6,117,159 A | 9/2000 | Huebsch et al. | |
| 6,120,524 A | 9/2000 | Taheri | |
| 6,139,564 A | 10/2000 | Teoh | |
| 6,171,320 B1 | 1/2001 | Monassevitch | |
| 6,171,329 B1 | 1/2001 | Shaw et al. | |
| 6,174,322 B1 | 1/2001 | Schneidt | |
| 6,179,863 B1 | 1/2001 | Kensey et al. | |
| 6,197,042 B1 | 3/2001 | Ginn et al. | |
| 6,206,907 B1 | 3/2001 | Marino et al. | |
| 6,228,096 B1 | 5/2001 | Marchand | |
| 6,231,561 B1 | 5/2001 | Frazier et al. | |
| 6,261,309 B1 | 7/2001 | Urbanski | |
| 6,277,140 B2 | 8/2001 | Ginn et al. | |
| 6,328,727 B1 | 12/2001 | Frazier et al. | |
| 6,334,865 B1 | 1/2002 | Redmond et al. | |
| 6,336,914 B1 | 1/2002 | Gillespie, III | |
| 6,342,064 B1 | 1/2002 | Koike et al. | |
| 6,350,274 B1 | 2/2002 | Li | |
| 6,355,052 B1 | 3/2002 | Neuss et al. | |
| 6,368,341 B1 | 4/2002 | Abrahamson | |
| 6,419,669 B1 | 7/2002 | Frazier et al. | |
| 6,425,911 B1 | 7/2002 | Akerfeldt et al. | |
| 6,436,088 B2 | 8/2002 | Frazier et al. | |
| 6,447,524 B1 | 9/2002 | Knodel et al. | |
| 6,482,179 B1 | 11/2002 | Chu et al. | |

* cited by examiner

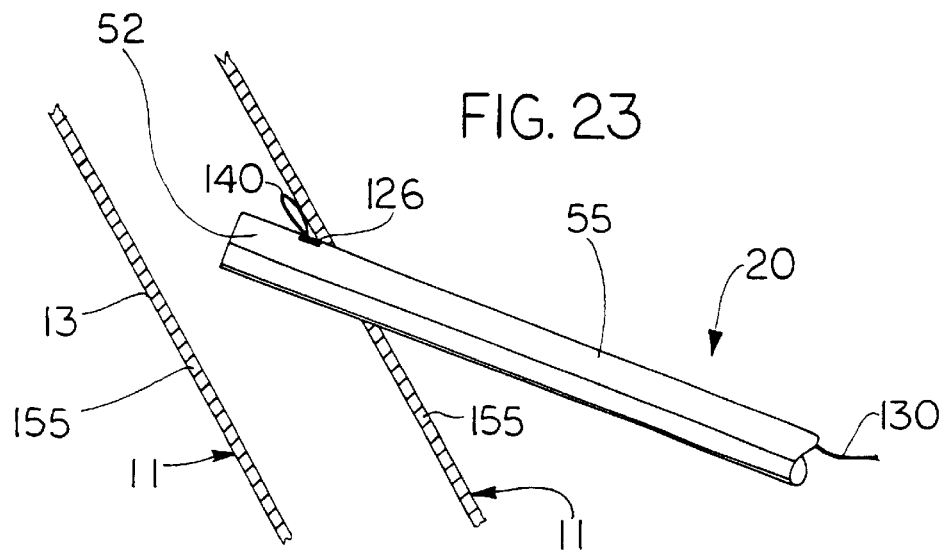
FIG. 23
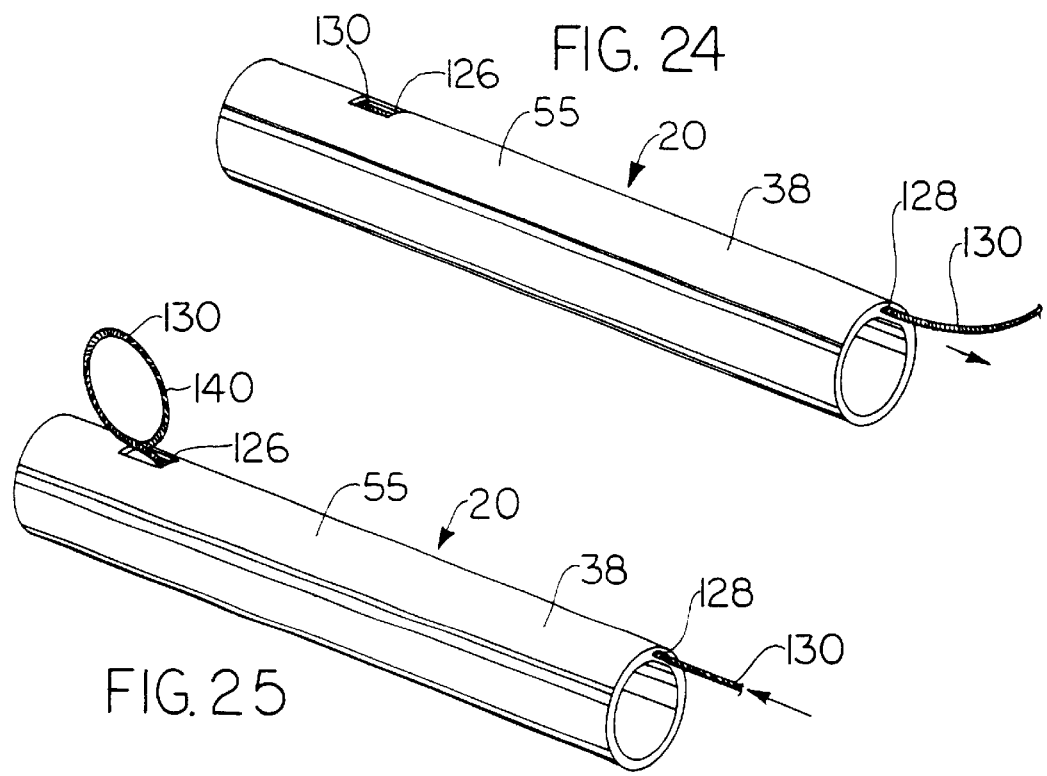
FIG. 24
FIG. 25

VASCULAR CLOSURE

CROSS-REFERENCE TO RELATED PATENT APPLICATION

This application is a continuation of application Ser. No. 09/659,648, filed Sep. 12, 2000 which claims priority from provisional application No. 60/153,736, filed Sep. 13, 1999.

BACKGROUND OF THE INVENTION

1. Field of the Invention

This invention relates to methods and apparatus for closing apertures in human and animal tissue and to methods and apparatus for inserting apparatus into such tissue to perform such closure functions.

2. Description of the Prior Art

During certain types of vascular surgery, catheters are inserted through an incision in the skin and underlying tissue to access the femoral artery in the patient's leg. The catheter is then inserted through the access opening made in the wall of the femoral artery and guided through the artery to the desired site to perform surgical procedures such as angioplasty or plaque removal. After the surgical procedure is completed and the catheter is removed from the patient, the access hole must be closed. This is quite difficult not only because of the high blood flow from the artery, but also because there are many layers of tissue that must be penetrated to reach the femoral artery.

Several approaches have used to close femoral access holes. Typically, manual compression by hand over the puncture site can be augmented by a sandbag or weight until the blood coagulates. With this approach it can take up to six hours for the vessel hole to close and for the patient to be able to ambulate. This increases time for the surgical procedure as well as overall cost of the procedure since the hospital staff must physically hold pressure and the patient's discharge is delayed because of the inability to ambulate. This is not an efficient use of either the patient's or staff's time. After some procedures, to close the vessel puncture site a clamp is attached to the operating table and the patient's leg; The clamp applies pressure to the vessel opening. The patient must be monitored to ensure the blood is coagulating, requiring additional time of the hospital staff and increasing cost of the procedure.

To avoid the foregoing disadvantages of manual pressure approaches, suturing devices have been developed. One such suturing device, referred to as "The Closer" and sold by Perclose, advances needles adjacent the vessel wall opening and pulls suture material outwardly through the wall adjacent the opening. The surgeon then ties a knot in the suture, closing the opening. One difficulty with this procedure involves the number of steps required by the surgeon to deploy the needles, capture the suture, withdraw the suture, and tie the knot, and cut the suture. Moreover, the surgeon cannot easily visualize the suture because of the depth of the femoral artery (relative to the skin) and essentially ties the suture knot blindly or blindly slips a pre-fabricated knot into position. Additionally, the ability to tie the knot varies among surgeons; therefore success and accuracy of the hole closure can be dependent on the skill of the surgeon. Yet another disadvantage of this suturing instrument is that the vessel opening is widened for insertion of the instrument, thus creating a bigger opening to close in the case of failure to deliver the closure system.

It would therefore be advantageous to provide an instrument which quickly and accurately closes holes in vessel walls. Such instrument would advantageously avoid the aforementioned time and expense of manual pressure, simplify the steps required to close the opening, and avoid widening of the opening.

SUMMARY OF THE INVENTION

The present invention overcomes the disadvantages and deficiencies of the prior art by, in one of its aspects, providing clip apparatus for closing a lumen aperture, particularly a vascular aperture, resulting from insertion of a surgical implement subsequent to completion of an invasive therapeutic procedure and withdrawal of the implement from the aperture where the apparatus includes an elongated strand comprising a central portion together with extremity portions extending from the central portion. The apparatus further involves tips of the extremity portions remote from the central portion being shaped to retain aperture peripheral tissue encountered thereby with the extremity portions having memory characteristics seeking to cause the extremity portions to curl towards and over one another about the central portion when the strand is in an unconstrained disposition, free of externally applied stress. Preferably, the apparatus is deployed in a two stage operation whereby the clip apparatus is initially deployed partially from a delivery apparatus with tips of the extremity portion contacting and the penetrating the interior surface of tissue of the vessel and acts to draw the aperture closed. In a second step the apparatus is fully dispensed from the delivery portion; tips of extremity portion of the apparatus do not penetrate the vessel tissue in the region about the aperture to be closed but act to draw the subcutaneous fascia on top of the outside aspect of the aperture. The two stage deployment of the closure apparatus results in a ratchet-type action by the deployment apparatus thereby providing extreme tactile sensitivity for the physician or other health professional handling the apparatus with resulting high sensitivity to the location of the apparatus and greater safety for the patient than otherwise possible.

In another of its aspects, this invention provides clip apparatus for closing a aperture, particularly a vascular aperture resulting from insertion of a surgical implement, into subsequent to completion of an invasive therapeutic procedure and withdrawal of the implement from the resulting aperture. In this aspect of the invention, the apparatus includes a plurality of elongated strands with each strand including a central portion and extremity portions extending from the central portion. Tips of the extremity portions remote from the central portion are shaped to retain aperture peripheral tissue encountered thereby. The extremity portions have memory characteristics seeking to cause the extremity portions to curl towards and about the central portion when the strand is in an unconstrained disposition, free of externally applied stress.

The clip apparatus may further include a band circumferentially enveloping the strands proximate the longitudinal midpoints of the strands for retaining the strand midpoints in close proximity to one another as the tip portions curl towards and about the midpoints. The band is preferably bonded to the strands.

The clip apparatus may further include a longitudinally elongated member extending from the central portions of grouped strands substantially in the longitudinal direction with respect thereto for facilitating gripping and guiding the strand portions of the clip member. The longitudinally elongated member is preferably rigid relative to the strand members.

In yet another of its aspects this invention provides a clip formed from a one piece integral strand, serving to close a lumen aperture such as a vascular aperture resulting from the insertion of a surgical instrument, where the clip includes an elongated strand of ribbon-like configuration having a central portion and extremity portions extending in opposite directions from the central portion. The central portion assumes a linear configuration and the extremity portions extending from the central portion assume configurations in which first parts of the extremity portions proximate the central portion curve towards one another and towards the central portion and second parts of the extremity portions relatively more remote from the central portion curve away from one another and from the central portion to position arcuate tips of the extremity portion sufficiently skew to the central portion that tissue around the periphery of the aperture which is punctured by the extremity portions is retained between the tip portions as the clip relaxes.

In yet another of its aspects this invention provides apparatus for closing an aperture such as a vascular aperture resulting from insertion of a surgical instrument into where the apparatus includes a telescoping tubular housing and clip apparatus resident within the housing for closing the aperture. In this aspect of the invention, the clip apparatus preferably includes a plurality of elongated strands with each strand having a central portion and extremity portions extending from the central portion. Tips of the extremity portions remote from the central portion are shaped to retain aperture peripheral tissue encountered thereby. The extremity portions have memory characteristics seeking to cause the extremity portions to curl towards and about the central portion of a respective strand when the strand is in an unconstrained disposition, free of externally applied stress.

In this aspect of the invention, the clip preferably further includes a band circumferentially enveloping the strands proximate the longitudinal midpoints thereof for retaining the strand midpoints in close proximity to one another as the tip portions curl towards and about the midpoints. In this aspect of the invention, the clip preferably further includes a longitudinally elongated member extending from the central portions of the strands substantially in the longitudinal direction with respect thereto and serving to facilitate gripping and guiding of the strand portions of the clip member. The strands, the band and the longitudinally elongated member are preferably bonded together integrally and reside in a housing. The housing is operable to dispense the clip from one end upon relative movement between telescoping sections of the housing.

In another aspect of the invention the housing may be tubular but not telescoping.

When the housing is telescoping, the housing may include at least two (2) telescoping sections and may operate to dispense the clip in a two (2) stage operation in which first relative movement between the telescoping sections results in a first portion of the clip being dispensed from the housing and additional relative movement between the telescoping section results in the remaining portion of the clip being dispensed from the housing.

In this aspect of the invention, the clip may further include a filament, positioned within the housing, connecting the clip to the housing with the filament preferably being connected to a longitudinal member portion of the clip. The filament is preferably flexible.

In this aspect of the invention, the longitudinal member portion of the clip preferably includes a loop formed therein thereby presenting a transverse passageway through the longitudinal member.

The housing preferably further includes a safety member for precluding second telescoping movement of the telescoping sections of the housing after the first telescoping movement until a safety member has been released.

In yet another of its aspects, this invention embraces a method for closing a vascular or other aperture resulting from, for example, insertion of the surgical implement thereinto subsequent to the completion of invasive therapeutic procedure and withdrawal of the implement from the aperture. The method includes providing an elongated strand comprising a central portion and extremity portions extending from the central portion with tips of the extremity portions remote from the central portion being shaped to retain aperture peripheral tissue encountered thereby with the extremity portions having memory characteristics seeking to cause the extremity portions to curl towards and over one another about the central portions when the strand is in an unconstrained disposition, free of externally applied stress.

The method further embraces dispensing the elongated strand from a tubular housing partially into the lumen aperture sufficiently far for the dispensed portion, consisting of the strand from an extremity to a central portion, to curl about and towards the strand central portion thereby to encounter tissue positioned immediately about the periphery of the aperture and to draw the aperture peripheral tissue radially inwardly relative to a longitudinal axis of the strand. In this aspect of the invention the method further embraces dispensing the remaining portion of the strand from a housing thereby permitting the remaining portion of the strand, from the central portion to a second strand extremity, to curl about and towards the central to of the vessel and drawing surrounding subcutaneous fascia radially inwardly relative to the longitudinal axis of the strand thereby substantially augmenting closure of the vessel, puncture site of the vessel external compression.

In yet another of its aspects this invention in a preferred embodiment provides clip apparatus for closing an aperture in tissue where the apparatus includes a first portion forming an arc, a second portion extending transversely from the first portion relative to the arc and a third portion extending from the second portion remotely from the first portion, with the third portion curving progressively relative to the second portion initially towards the first portion and then towards the second portion with a tip of the third portion being adapted for piercing and retaining tissue encountered thereby. In this aspect the invention further preferably includes at least two third portions extending from the second portion at a common position with the third portions curving progressively first towards the first portion and then towards the second portion and each other.

In this aspect the invention may further embrace clip apparatus having a pair of second portions respectively connected to parts of the first portion separated by the arc and extending transversely to the arc in a common direction relative thereto with a pair of third portions extending from respective ones of the second portions, curving progressively first towards the first portion and then simultaneously towards the second portion and each other.

In this aspect of the invention extremities of the third portions desirably contact the second portions, the second portions are preferably linear and the curved segments of the third portions are preferably separated by linear segments.

In this aspect of the invention the first portion is preferably configured as a figure eight.

In this aspect of the invention the second portion preferably extends away from the first portion perpendicularly to a plane of the arc.

When the first portion is configured as a figure eight the second portion preferably extends away from the center of the figure eight configuration.

In this aspect of the invention the first portion further preferably has at least two arcs separated by a straight segment. Further, at least one of the arcs preferably subtends an angle of greater than one hundred eighty degrees.

Still further, the arcs preferably each have straight segments adjoining the ends of the arcs and connecting with the second portions. In this aspect of the invention both of the arcs preferably subtend an angle of greater than one hundred eighty degrees. The second portions are preferably straight and the linear segments of the third portions are preferably straight.

In another aspect this invention provides apparatus for closing an aperture in tissue where the apparatus includes an elongated unitary strand having a central portion and extremity portions extending from the central portion. Tips of the extremity portions remote from the central portion are preferably pointed to engage and retain tissue encountered thereby. The strand is preferably configured so that the tips are at ends of respective curved portions and face towards one another when the clip is in an unconstrained state, free of internal stresses. The strand preferably has a memory characteristic causing the clip, when unconstrained, to seek to return to an unstressed state with the tips seeking to draw together sufficiently to retain tissue engaged by the tips for closing the aperture and retaining the subcutaneous tissue at the exterior surface of the aperture causing external compression by the tips.

In this aspect of the invention the strand preferably further includes a pair of mid-portions intermediate the tips and the central portion with the central portion disposed in a first plane and the mid-portion disposed in a plane transverse to the first plane. The mid-portion preferably has a linear part connected to the central portion and extending transversely therefrom.

Preferably, the central portion is configured to have at least one loop subtending an angle of at least about 180 degrees.

In this aspect of the invention the loop is preferably closed by overlap of the strand upon itself, the central portion preferably lies in a plane, the extremity portions are preferably in a plane transverse to the plane of the central portion and the tips are preferably at ends of the curved portions of the strand, with the tips being closer to the central portion than to the curved portions of the strand supporting the tips.

In this aspect of the invention an upper portion of the apparatus is preferably configured as a figure eight. This apparatus aspect of the invention further has the strand preferably having a mid-portion intermediate the tips and the central portion, extending transversely to the central portion with the tips facingly opposing one another on either side of the mid-portion and pointing away from the central portion in a common direction. The mid-portion is preferably perpendicular to the central portion; the central portion preferably includes a plurality of loops.

In this aspect of the invention the strand is preferably metal and is most preferably a filament. The strand may include at least two filaments.

In this apparatus aspect of the invention the central portion may include at least two preferably co-planar loops.

In another aspect, this invention provides apparatus for inserting a surgical clip which is housed therewithin into tissue to close an aperture in the tissue where the apparatus includes a first handle portion housing a tubular member and having a hand grip extending transversely therefrom where the tubular member is connected to the handle portion and extends generally longitudinally from the handle portion. Surgical clip positioning means are preferably provided at a distal end of the tubular member remote from the handle. A clip loading wire is preferably provided looping around the clip, residing at least partially within the tubular member at a distal end thereof, extending along the length of the tubular member and exiting from the handle portion at a proximate end of the tubular member. The apparatus preferably further includes a clip pusher member movable axially within the tubular member through a range of motion from a first through an intermediate to a second position for displacing the clip from within the tubular member in two stages. The clip is housed within the apparatus and is ready for insertion into the lumen when the pusher member is at the first position. The clip extends partially from the tubular member when the pusher member is at the intermediate position; the clip is separated from the apparatus and presumably within the tissue of interest closing the targeted aperture when the pusher member is at the second position.

In this aspect of the invention the surgical clip insertion apparatus preferably further includes a ring connected to the wire with the ring being detachably mounted on the handle portion at the proximate end of the tubular member. The ring facilitates hand powered movement of the loading wire to draw the clip at least partially into the tubular member.

Preferably in this aspect of the invention the clip positioning means serves to position the clip angularly within the tubular member; most desirably the clip positioning means are slots formed in the tubular member with the slots communicating with the distal end of the tube. Most desirably the slots correspond in number to the number of tissue penetrating points of the surgical clip housed within the apparatus. Further desirably the clip positioning means served to position the surgical clip longitudinally within the tubular member.

In yet another aspect the invention provides apparatus for inserting a surgical clip into tissue to close an aperture in tissue where the apparatus includes a first handle portion, a tubular member connected to the handle portion and extending generally transversely therefrom, a clip loading member pivotally connected to the tubular member and moveable between positions at which the clip is loaded into the apparatus and at which the clip is housed within the apparatus and ready for insertion into the tissue and a clip trigger member which is moveably axially within the tubular member through a range of motion from a first through an intermediate to a second position for displacing the clip from the tubular member in two stages. The clip is desirably housed within the apparatus and ready for insertion into tissue when the trigger is at the first position. The clip preferably extends partially from the tubular member when the trigger is at the second position. The clip is preferably separated from the apparatus and presumably inserted into tissue and closing the aperture of interest when the trigger is at the third position.

BRIEF DESCRIPTION OF THE DRAWINGS

In FIG. 7 the clip is illustrated at the intermediate position from which the physician or other attending healthcare professional may withdraw the clip back into the position illustrated in FIG. 6 or may continue to eject and deploy the clip into the position illustrated in FIG. 8 whereby tip members of the clip have penetrated the vessel wall and served to at least substantially close an aperture therein.

In FIG. 8 the clip is illustrated fully deployed and ratcheting operation is complete.

FIG. 23 is a broken, partially sectioned side view of another embodiment of a clip delivery member in accordance with the invention in place within tissue ready to eject a clip into place to close an aperture in a vessel.

FIG. 24 is an isometric view of a portion of the clip delivery member illustrated in FIG. 23.

FIG. 25 is an isometric view of a portion of the clip delivery member illustrated in FIGS. 23 and 24 showing a clip positioning loop extending from the exterior of the clip delivery member.

FIG. 31 is a broken sectional view of the clip illustrated in FIGS. 29 through 31 taken at lines and arrows 32—32 in FIG. 31.

DETAILED DESCRIPTION OF THE INVENTION

Figure 1:
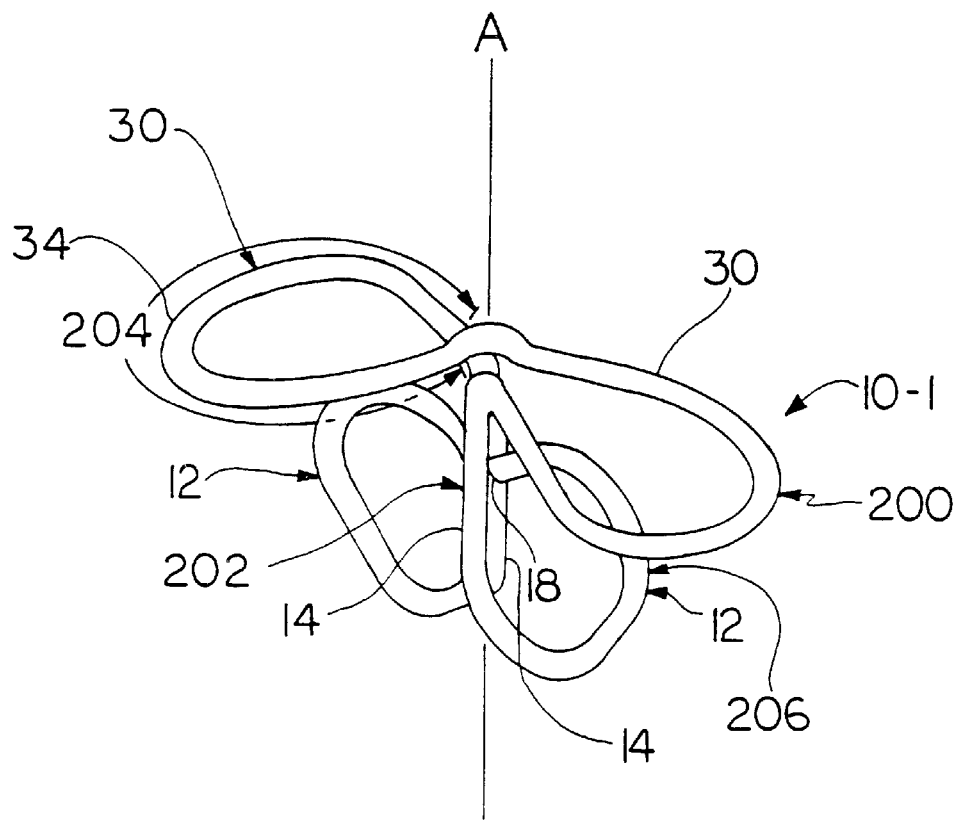
FIG. 1 is an isometric view of a surgical tissue closure clip manifesting the preferred embodiment of the clip aspect of the invention, with a vertical axis designated "A" shown for reference purposes.

This invention provides apparatus and methods for closing a tissue aperture, particularly a vascular or vessel (the two terms being used interchangeably herein) aperture, resulting from insertion of a surgical implement or from accidental trauma or from disease. The invention embraces both apparatus and method aspects of devices for closing a vascular aperture and apparatus and method aspects of second devices for delivering the closure apparatus into the aperture being closed. The closure apparatus preferably has at least a portion formed of a memory material, preferably metal, which, when deformed from its stress-free state, seeks to return to the stress-free state. The stress-free state corresponds to the state at which the apparatus has closed an aperture in a vessel. In conjunction with the delivery apparatus of the invention, the closure apparatus provides a two-step, ratchet-like action closing the aperture of interest while acting to draw a subcutaneous tissue exterior to the vessel towards the aperture simulating manual compression.

In the drawings tissue closure clips in accordance with the invention are designated generally 10. Four different embodiments of the invention are respectively identified 10-1, 10-2, 10-3 and 10-4 in the drawings. The embodiment of the tissue closure clip identified as 10-1 in FIGS. 1 through 10, 13 and 14 is the preferred embodiment of tissue closure clip apparatus in accordance with the invention.

In the first embodiment in which the clip is designated generally 10-1 a central portion 14 leads into a pair of upper horizontally extending side arms 30 and into two lower elongated strand portions 12 that function to at least contact and preferably pierce the vessel wall and close the aperture.

Referring to FIGS. 1 through 5, 13 and 14, clip 10-1 for closing an aperture in a vessel includes a first portion 200 forming an arc. A second portion 202 extends transversely from first portion 200 relative to the arc where the arc is designated generally 204 in the drawings. A third portion 206 extends from second portion 202 remotely from first portion 200 and curves progressively, relative to second portion 202, initially towards first portion 200 and then towards second portion 202. A tip 18 of third portion 206 is adapted for piercing and retaining tissue encountered thereby.

Figure 13:
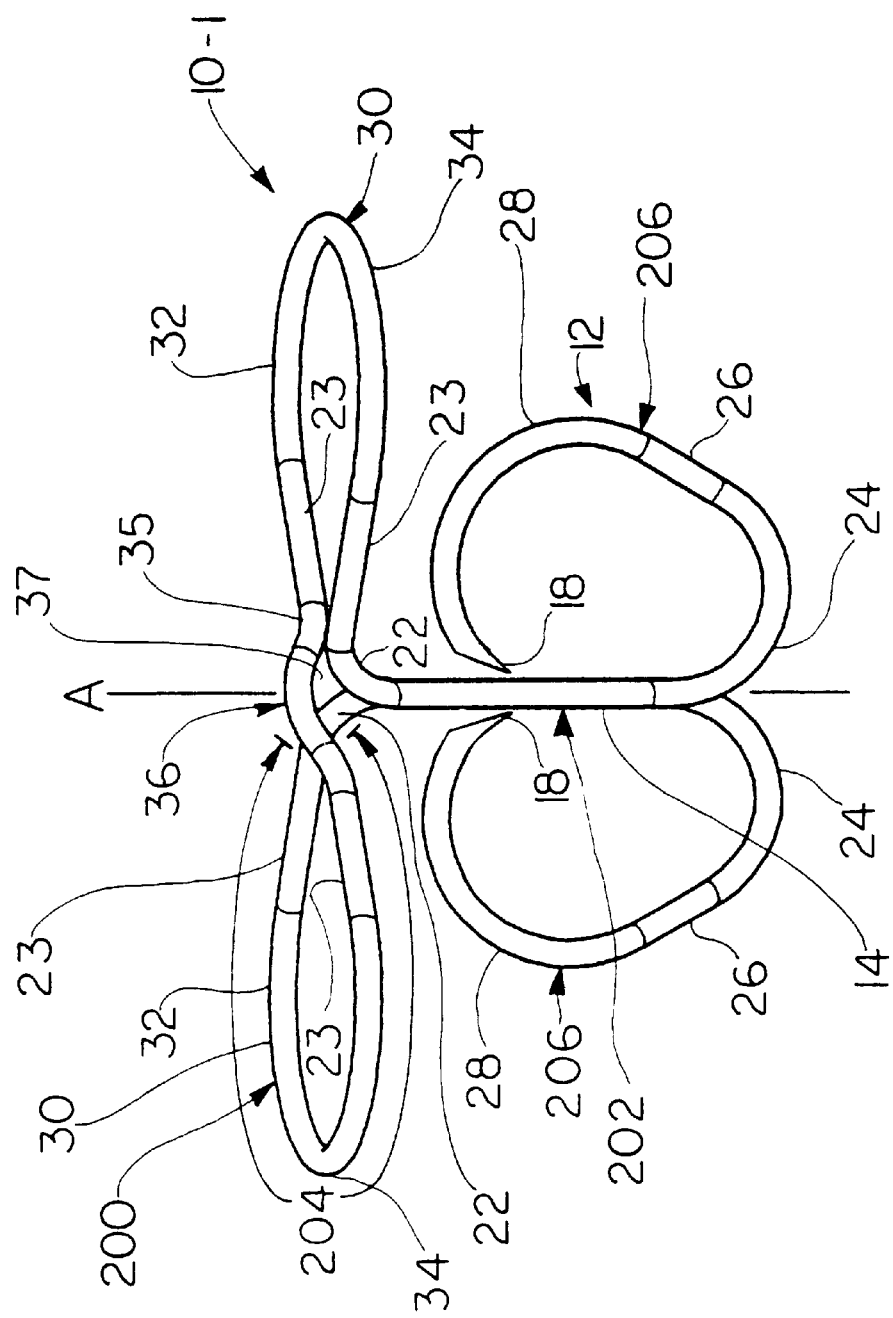
FIG. 13 is an enlarged isometric view of a preferred embodiment of a clip shown in FIGS. 1, 2, 3, 4 and 5 with lines added to the surface to facilitate identification.
Figure 14:
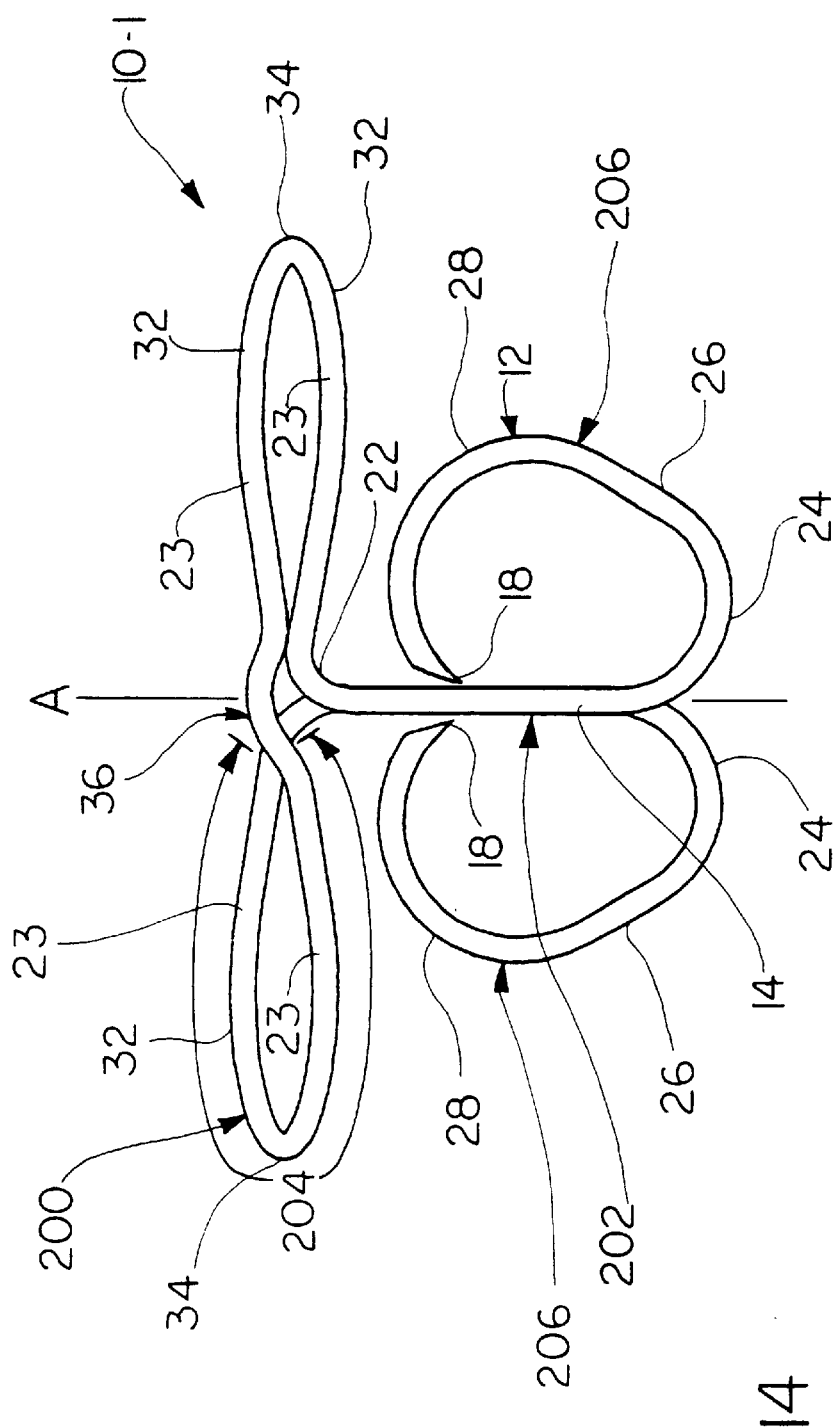
FIG. 14 is identical to FIG. 13 but without the added surface lines.

In the drawings and particularly in FIG. 13 it is seen that second portion 202 embraces central portion 14. Third portion 206 embraces a pair of transition portions 24 which are located between central portion 14 and a central segment 26 of third portion 206. Still referring to FIG. 13, third portion 206 further includes a curved transition portion 28 extending between third portion central segment 26 and a tip 18.

Clip 10-1 is preferably formed from a single strand of material and hence includes two third portions 206 formed at respective ends of the strand. Each third portion 206 includes a transition portion 24, a central segment 26, a transition portion 28 and a tip 18, all as illustrated in FIG. 13.

Still referring to the same drawing figures and particularly to FIG. 13, first portion 200 includes a pair of curved transition junctures 22 connecting first portion 200 with second portion 202, namely with central portion 14. Each transition juncture 22 leads in turn to a preferably straight segment 23.

Referring to FIGS. 15 through 19 illustrating the embodiment of the clip designated generally 10-2, a central stem 76 extends from an upper saddle configuration and supports four elongated extending portions 89 that function to pierce the vessel wall and close the aperture.

Figure 20:
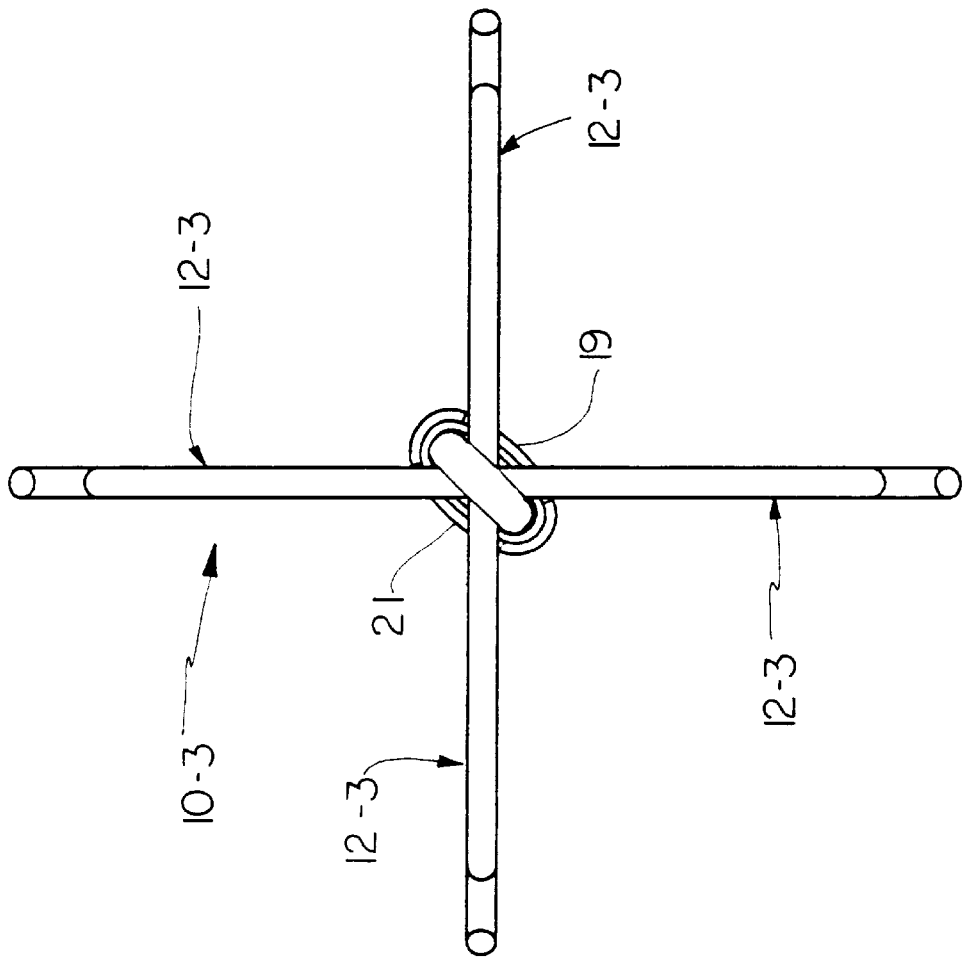
FIG. 20 is a top view of a third embodiment of a tissue closure clip manifesting aspects of the invention.
Figure 21:
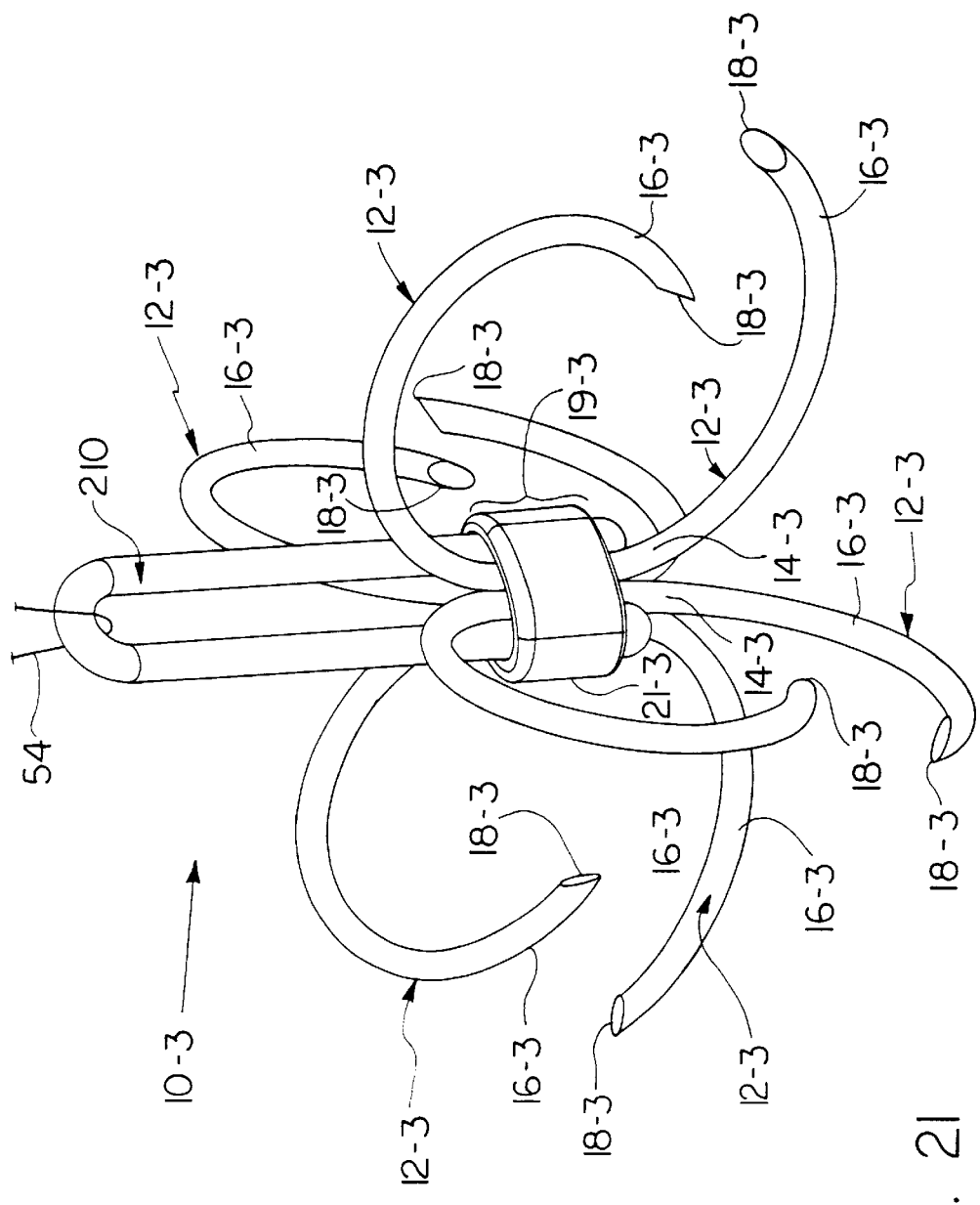
FIG. 21 is an isometric view of the closure clip illustrated in FIG. 20.
Figure 22:
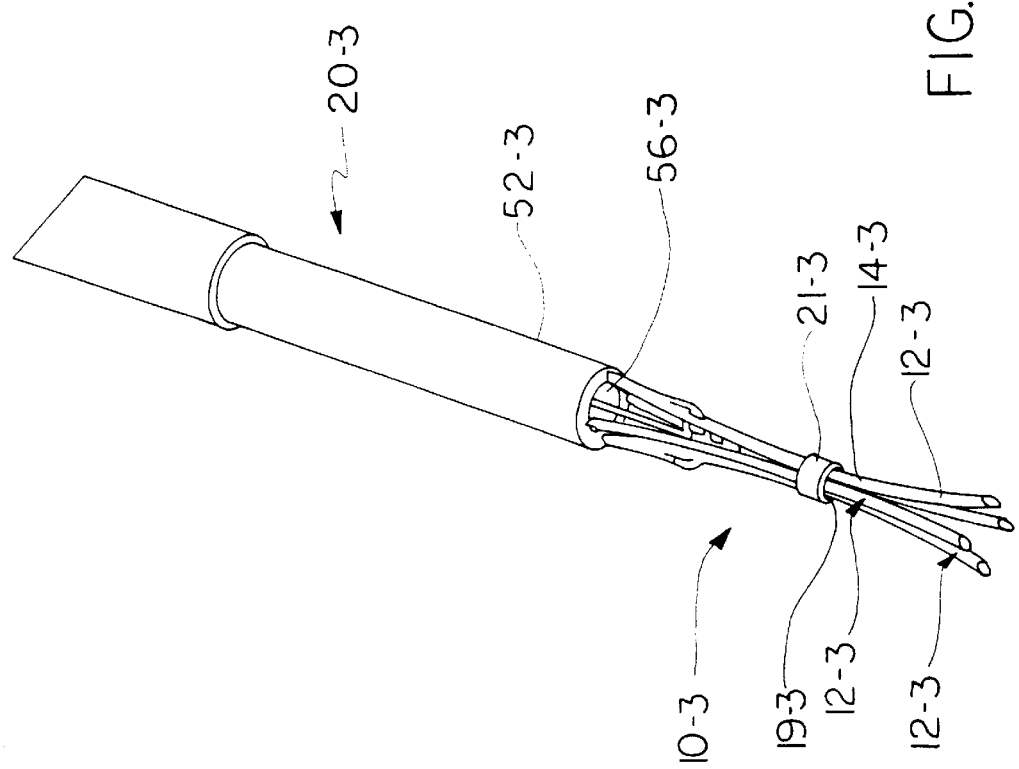
FIG. 22 is an isometric view of the tissue closure clip illustrated in FIGS. 20 and 21 being dispensed from a portion of a telescoping housing.

Referring to FIGS. 20 through 22 in which the clip is designated generally 10-3, a central region 19 supports a plurality of upper and lower elongated strands 12-3 functioning to pierce the vessel wall from above and below to close the aperture.

Figure 2:
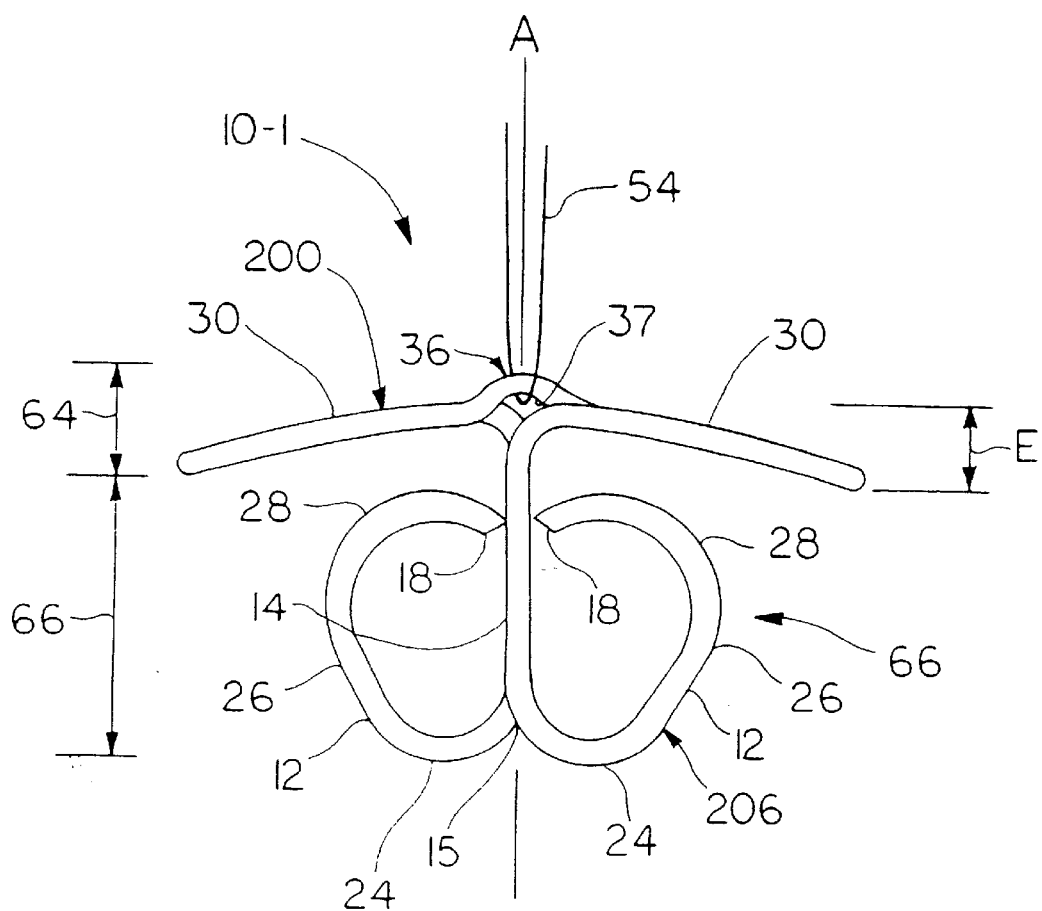
FIG. 2 is a front view of the clip illustrated in FIG. 1 with vertical axis A and a horizontal axis shown for reference purposes and with reference lines 64 and 66 designating respective upper and lower portions of the clip.

Clip 10-1 is preferably memory metal and has an unstrained conformation illustrated in FIG. 1. Referring to FIG. 2, clip 10-1 maybe be considered to have upper and lower halves designated 64 and 66 respectively.

Central portion 14 is coincident with a central vertical axis designated A and drawn in FIG. 2 for reference purposes. Central portion 14 extends into both upper half 64, wherein extending side arms 30 extend horizontally and upwardly from central portion 14, and into lower half 66 wherein third portions 206 extend downwardly and outwardly from central portion 14. Central portion 14 includes two preferably tangentially contracting segments, where the position of tangency is designated 15.

Figure 4:
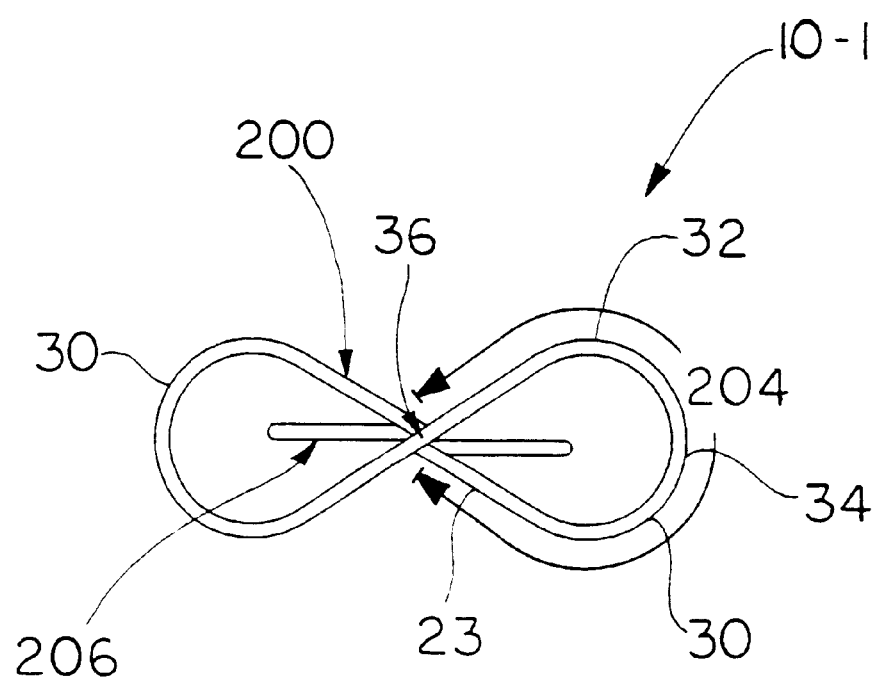
FIG. 4 is a top view of the clip illustrated in FIGS. 1, 2 and 3.
Figure 5:
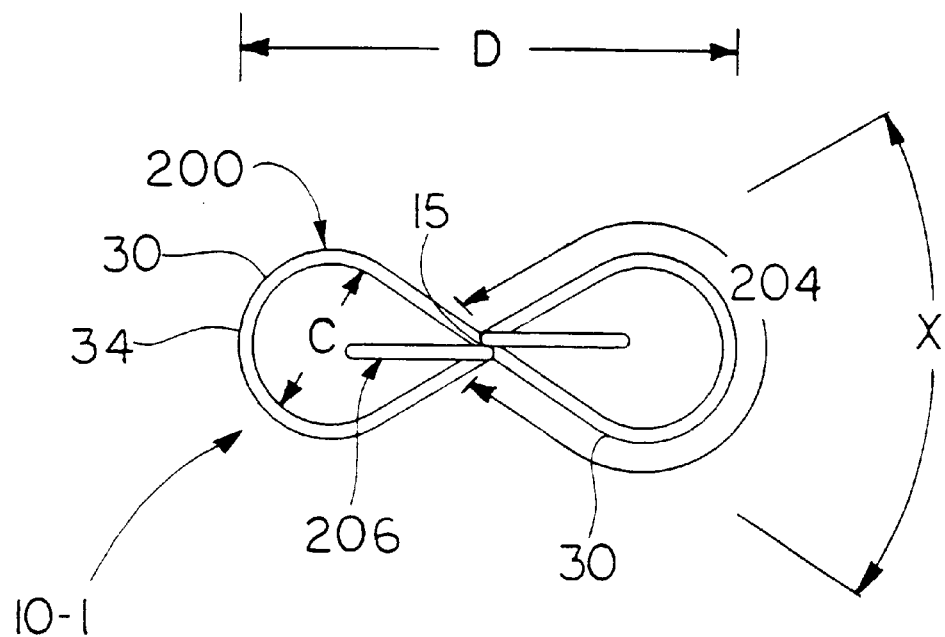
FIG. 5 is a bottom view of the clip illustrated in FIGS. 1, 2, 3 and 4.
Figure 8:
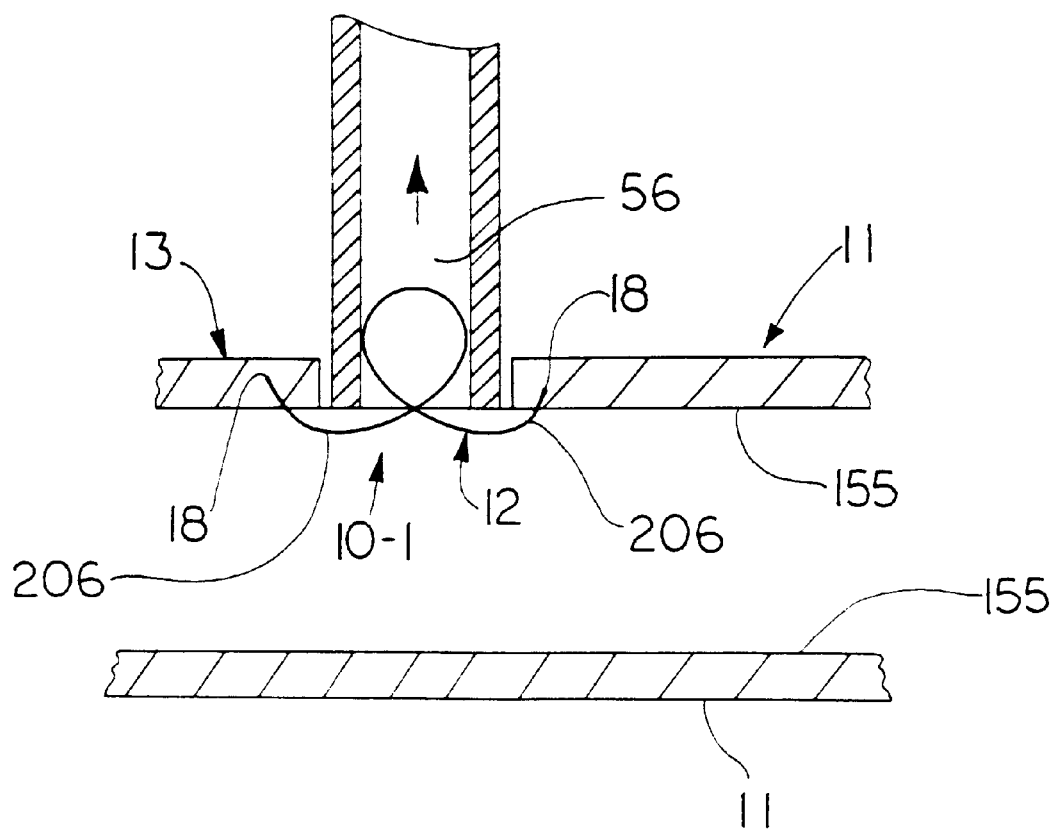
FIG. 8 is a broken vertical section similar to FIG. 7 of a preferred embodiment of the clip shown in FIG. 6 penetrating a wall of the vessel as the clip delivery apparatus is withdrawn.

Referring to FIGS. 4 and 5, upper half 64 comprises a FIG. 8 configuration forming a central crossover juncture 36 which defines commencement of horizontally extending side arms 30 denoted by the brackets in FIG. 4.

Preferably, angular expansion of horizontally extending side arms 30 from the central midpoint within the FIG. 8 configuration is, as indicated by angle X in FIG. 5, approximately 62.7°. In the preferred embodiment clip 10-1 preferably has a loop diameter of about 0.15 inches denoted by dimensional indicator C in FIG. 5 and a horizontal crosswidth of about 0.441 inches, denoted by dimensional indicator D in FIG. 5.

Figure 9:
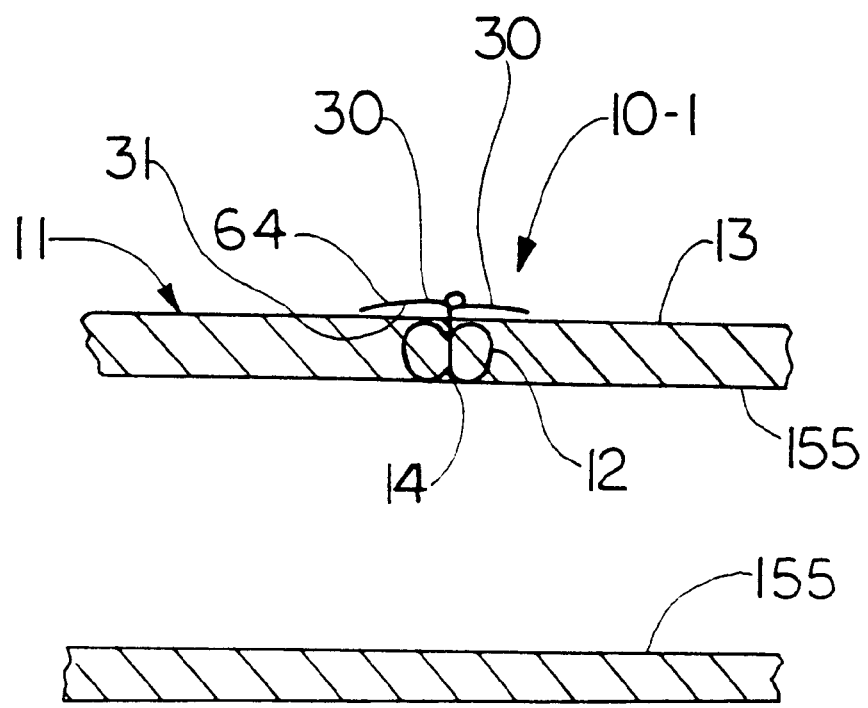
FIG. 9 depicts a preferred embodiment of the clip in accordance with the invention shown in FIGS. 1 through 8 in position within a vessel wall in an unconstrained configuration, closing an aperture in the wall.

As is apparent from FIG. 9, when clip 10-1 has deployed and closed an aperture in a vessel 11, upper half 64 preferably extends externally to now closed vessel 11, horizontally extending side arms 30 reside proximate to and preferably contact exterior surface 13 of vessel 11 and undersides 31 of horizontally extending side arms 30 preferably contact exterior surface 13.

Lateral extremities of upper half 64 preferably are about 0.037 inches below the center of upper half 64, namely crossover junctures 36, as indicated by dimensional indicator E in FIG. 2.

Figure 9A:
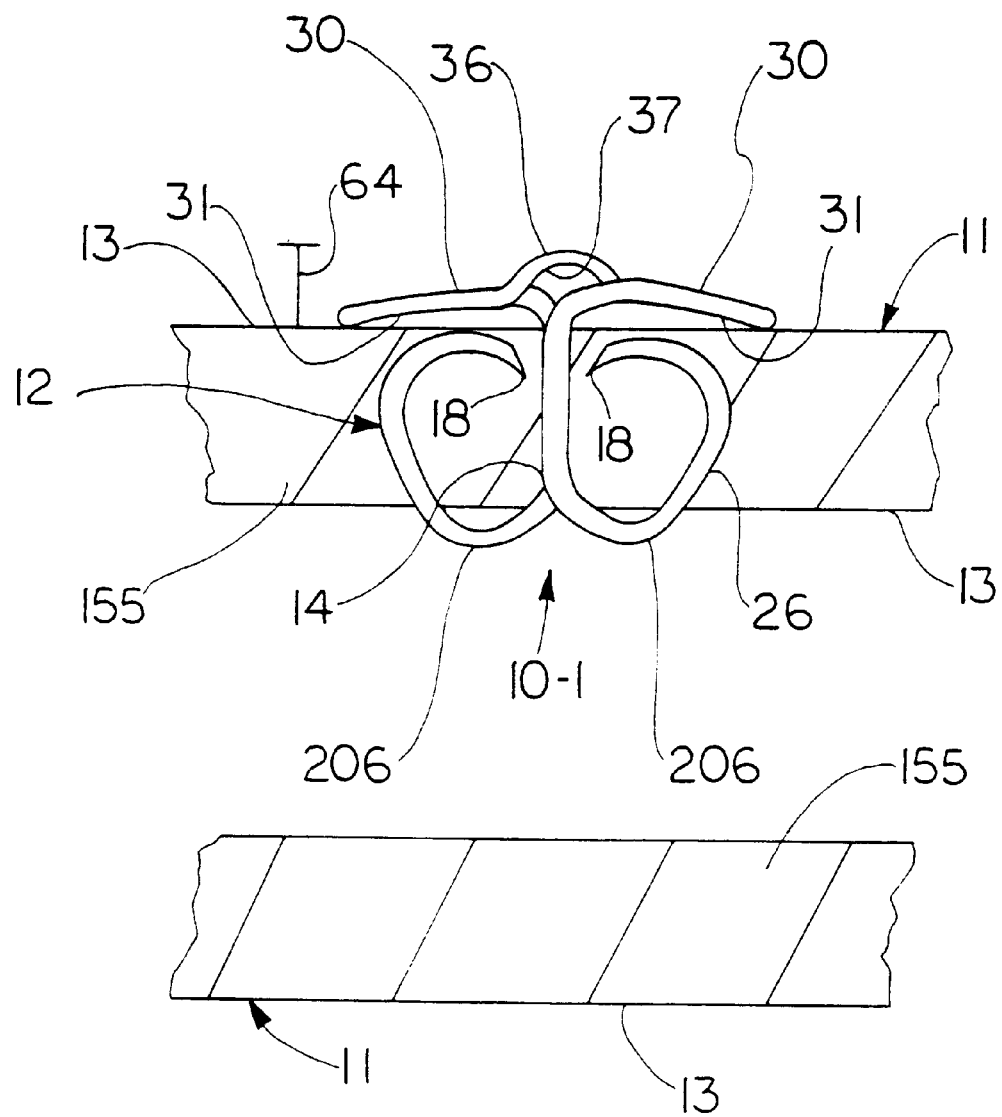
FIG. 9A is an enlarged view of the clip depicted in FIG. 9 showing the clip within a vessel wall in an unconstrained configuration at least substantially closing an aperture in the vessel wall.

Lower half 66 includes a part of central portions 14-1 extending leading into elongated portions of strand 12-1 which define third portion 26-1 and function to pierce the tissue of vessel 11, closing the aperture. Referring to FIG. 9A the parts of deployed elongated strand 12 defining third portion 206 preferably extend within the tissue surrounding the aperture closed in vessel 11.

Referring to FIG. 13, clip 10-1 comprises several transition portions. Coincident with central vertical axis A is central portion 14, which preferably includes two vertical segments which lead to third portion 26 defined in part by two curved transition portions 24. Central portion 14 also leads to first portion 29 which is defined in part by upwardly curved transition portions 22 leading to horizontally extending side arms 30.

Figure 3:
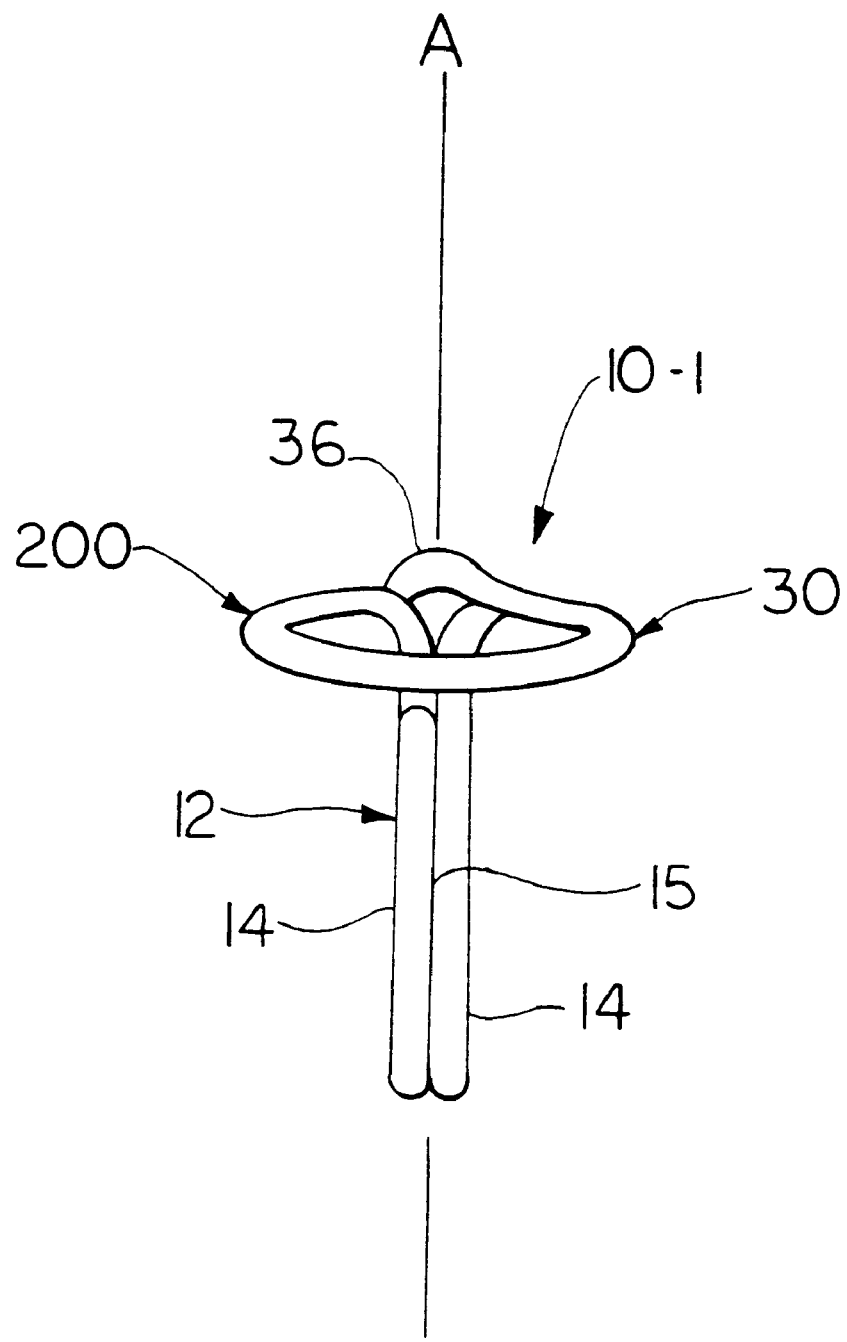
FIG. 3 is a side view of the clip illustrated in FIGS. 1 and 2, looking from left to right in FIG. 2.

Referring to FIG. 3, central portion 14 comprises two vertical segments; a point of tangency 15 between those segments is coincident with vertical axis A. FIG. 3 illustrates that the two vertical segments comprising central portion 14 preferably are mutually offset equidistantly from vertical axis A; these portions of elongated strand 12 are preferably separated by one hundred eighty degrees (180°).

Referring to FIGS. 4 and 5, third portions 206 of elongated strand 12 preferably are mutually offset and preferably equidistant from one another on opposite sides of vertical axis A which is not shown in FIGS. 4 and 5.

Referring to FIG. 13, transition portion 24 defines the beginning of the third portions 206 of elongated strand 12, which initially extend downwardly and then curve upwardly leading into upwardly extending central segment 26 of third portion 206. Upwardly extending central segment 26 defines transition from curved portion 24 to the curved transition portion 28 of third portion 206. Curved loop transition portion 28 leads to the ends, namely the tip or terminus end portions 18, of elongated strand 12. Tips 18 preferably are tapered to a sharp point functioning to easily penetrate tissue.

Transition junctures 22 lead to straight segments 23 which in turn lead to the beginning of outwardly curved portions 32 of horizontally extending side arms 30, all being a part of first portion 200. Two outwardly curved portions 32 preferably extend horizontally and hence transversely with respect to preferably vertical central portion 14 to define horizontally extending side arms 30 wherein transition portions 34 define the radial outward extremities of curved portions 32.

Figure 11:
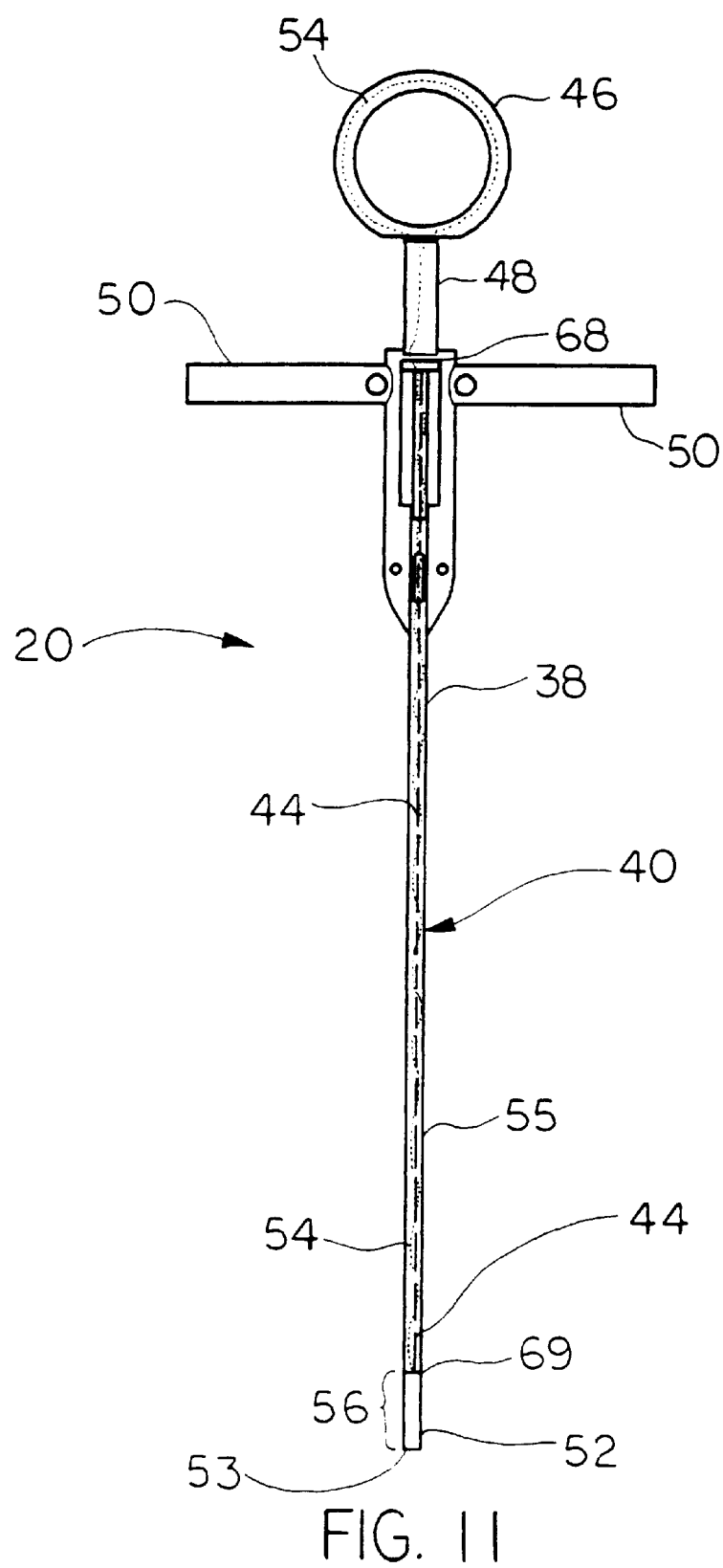
FIG. 11 is a front elevation of a preferred embodiment of a clip delivery member in accordance with the invention, partially broken away to reveal interior details.
Figure 12:
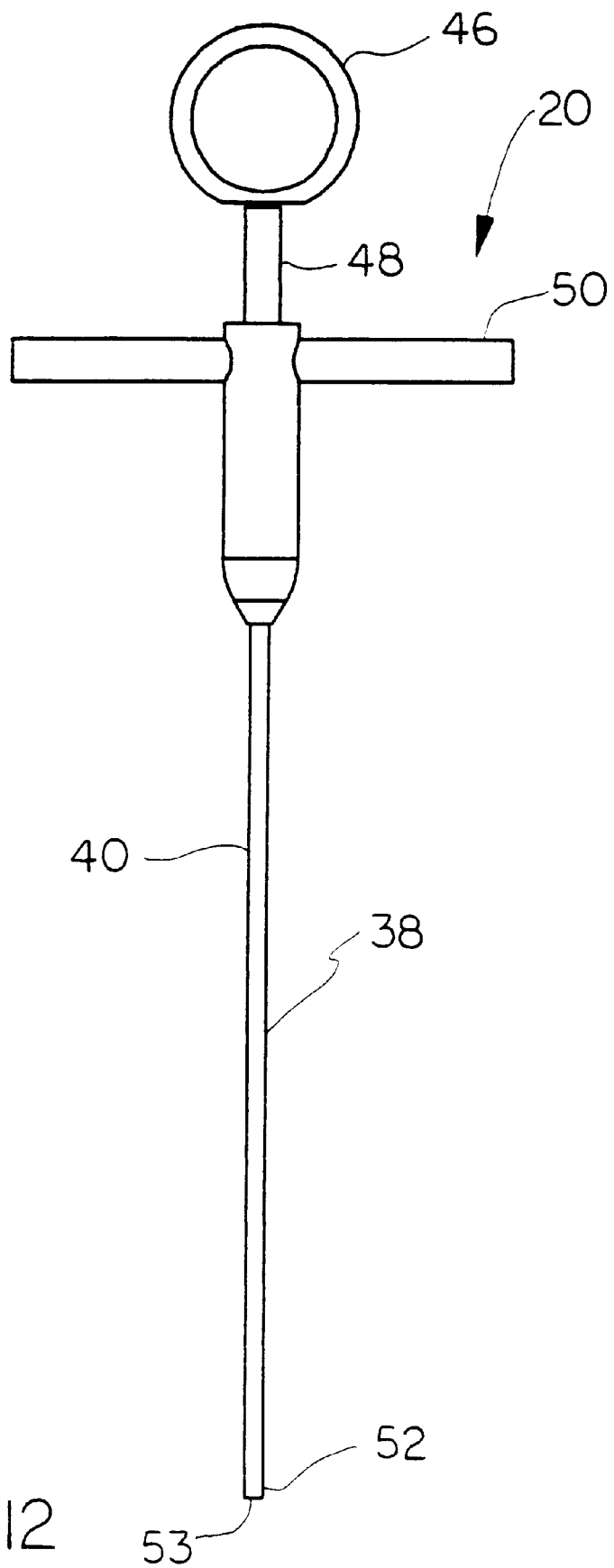
FIG. 12 is a front elevation of the preferred embodiment of the clip delivery member illustrated in FIG. 11.

FIG. 2 illustrates the preferably slight downward curvature of preferably substantially horizontally extending side arms 30. Coincident with vertical axis A is an upwardly curved crossover juncture 36 creating a catch 37 for insertion of a guide wire 54 therethrough for drawing clip 10-1 into an ejection chamber 56 such as shown in FIG. 11.

As illustrated in FIG. 13 transition between preferably substantially horizontally extending side arms 30 and crossover juncture 36 is defined by an upwardly curved portion 35 defining catch 37.

Figure 6:
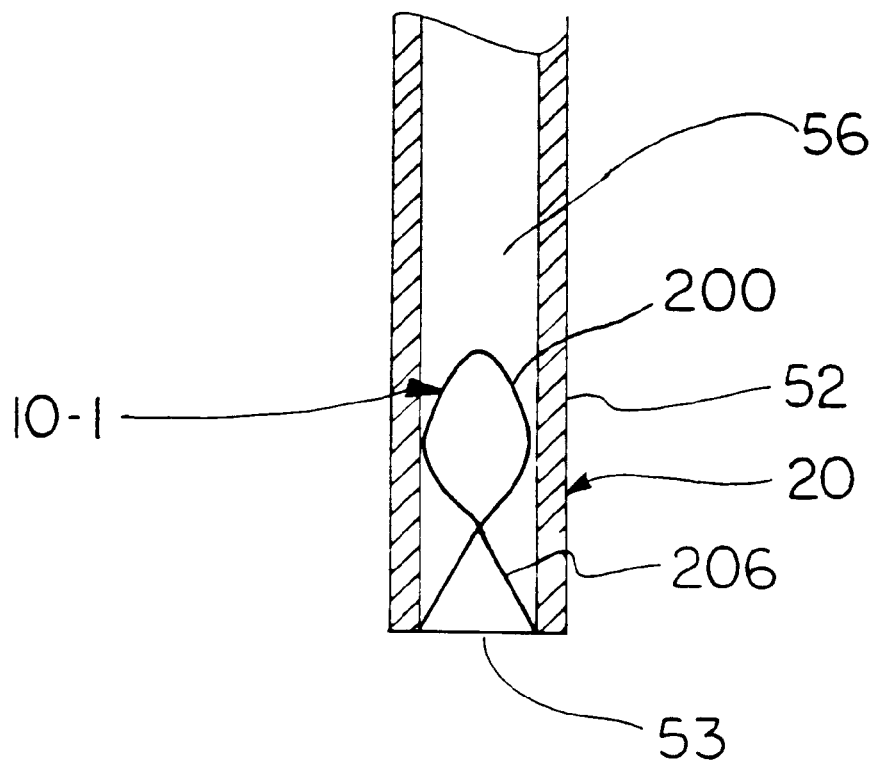
FIG. 6 is a broken vertical section of a preferred embodiment of a clip in accordance with the invention as illustrated in FIGS. 1 through 5 in position ready for deployment from a clip delivery member manifesting the preferred embodiment of delivery apparatus in accordance with the invention.

Referring to FIG. 6 when clip 10-1 is loaded into a device for deployment of clip 10-1 to close a vessel aperture, clip 10-1 is in a strained extended configuration, as illustrated.

A front end 52 of a suitable clip delivery member 20 is depicted in FIG. 6. Clip 10 is shown within ejection chamber 56 which accommodates clip 10-1 in a constrained, narrow, extended configuration. Front end 52 is defined by a hollow tubular opening 53 of clip delivery member 20 wherein hollow tubular opening 53 facilitates ejection of medical clip 10-1.

Figure 7:
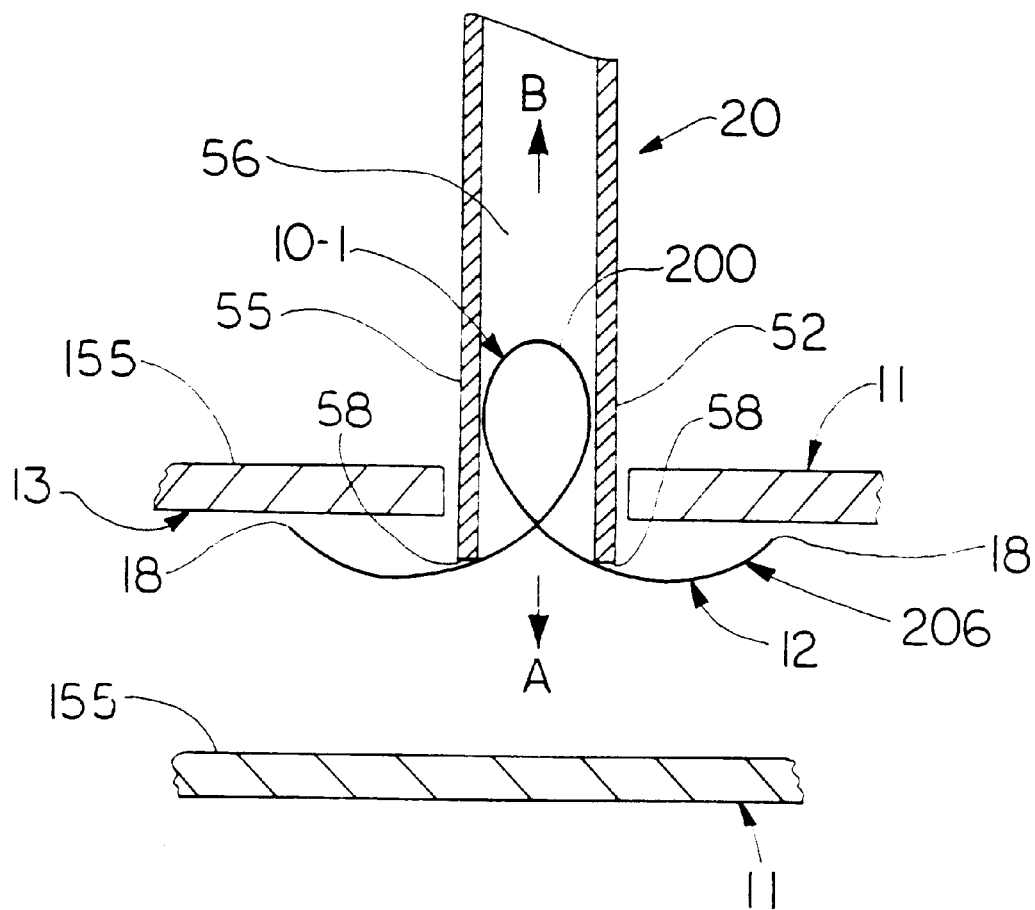
FIG. 7 is a broken vertical section of a preferred embodiment of a clip in accordance with the invention as illustrated in FIG. 6 in the process of being deployed from within a clip delivery member and inserted into a vessel.

FIG. 7 shows insertion of front end 52 of clip delivery member 20 with clip 10-1 therein into an aperture within a vessel 11. As illustrated in FIG. 7, commencement of ejection to deploy clip 10-1 moves clip 10-1 towards front end 52 of ejection chamber 56.

In FIG. 7 clip 10-1 is depicted in the process of being deployed at the intermediate position. FIG. 6 illustrates clip 10-1 in the initial position. Clip 10-1 is pushed by push rod 44 acting in response to thumb pressure applied to firing button 48 and moves from the position illustrated in FIG. 6 to a position at which third portion 206 of clip 10-1 extends outwardly from ejection chamber 56 while first portion 200 of clip 10-1 remains within ejection chamber 56. The intermediate position of clip 10-1 defining the first of the two ratchet-like stages of clip deployment is illustrated in FIG. 7 with clip 10-1 at position to initate the second stage of deployment with third portion 206 of clip 10-1 extending radially outwardly as clip 10-1 endeavors to relieve itself of internal stresses. As a result tips 18 have encountered a surface portion of vessel 11 at the position illustrated in FIG. 7. As clip 10-1 is further ejected from ejection chamber 56 in the direction indicated by arrow A in FIG. 7 third portions 206 continue to curve, seeking to reach the position illustrated substantially in FIG. 8. As third portions 206 continue to curve, tips 18 penetrate wall 15 of vessel 11 and urge the respective penetrated portions of wall 15 and vessel 11 towards one another, radially inwardly with respect to axis A in FIG. 1. Continued curvature of third portions 206 as tube 55 is removed from vessel 11 permits third portions 206 to reach their configuration whereby they are at least substanially free of internal stresses, as shown generally in FIG. 9A thereby closing the aperture of interest in vessel 11 as illustrated in FIGS. 9 and 9A.

In the event the physician or other attending health professional wishes to reposition clip 10-1 in the midst of the procedure, the physician or other attending health professional may draw clip 10-1 back into tube 55 in the direction indicated by arrow B in FIG. 7 by pulling on pull ring 46 having wire 54 connected thereto, neither of which are illustrated in FIGS. 6 through 9A but which preferably runs through tube 55 to ring 46 in FIG. 11. Of course, in the event the physician or other health professional has disconnected wire 54 from pull ring 46 the only course of action remaining for the physician or other attending health professional is to advance push rod 44 thereby fully deploying clip 10-1 in the position to close the aperture as illustrated in FIGS. 9 and 9A.

Grooves 58 in front end 52 of clip delivery member 20 guide third portions 206, which normally extend horizontally when clip 10-1 is deployed and has relieved itself of internal stresses, when the clip is loaded into delivery member 20. Movement of clip 10-1 is depicted by an arrow within ejection chamber 56 denoting the downward direction of ejection of clip 10-1 from ejection chamber 56.

Figure 10:
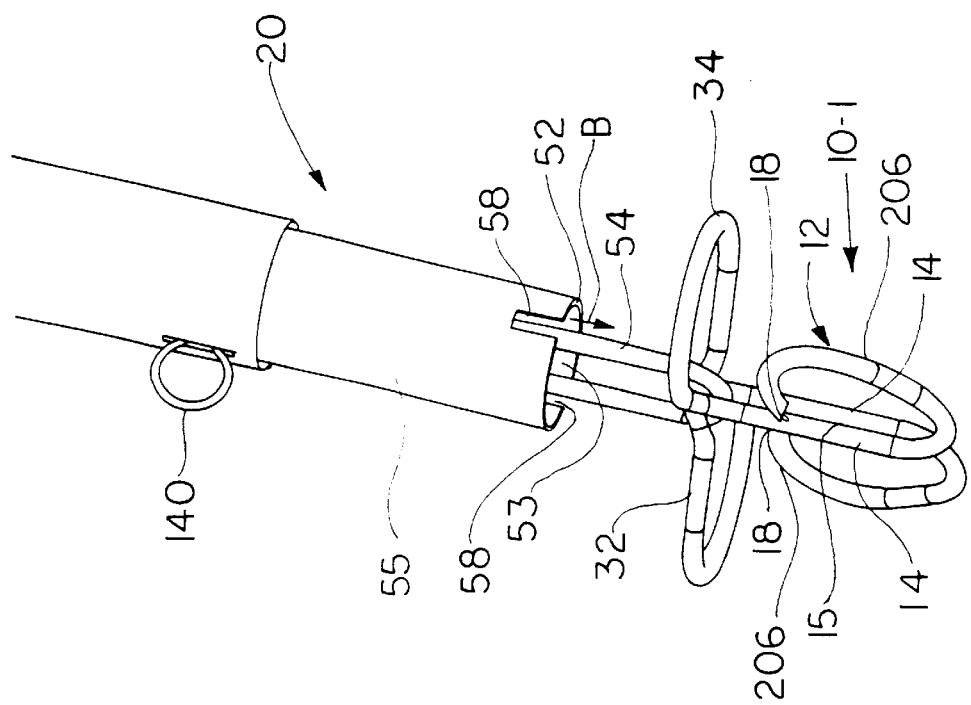
FIG. 10 is an enlarged broken isometric view of the front end of clip delivery member and clip as illustrated in FIGS. 1, 2, 3, 4 and 5 in accordance with the invention.

An enlarged view of front end 52 of clip delivery member 20 shown in FIG. 10 illustrates grooves 58.

Deployment of clip 10-1 from within ejection chamber 56 into a vessel is depicted in FIG. 8 wherein tips 18 of elongated strand 12 are shown advancing upwardly and laterally thereby piercing peripheral tissue. Preferably, tips 18 taper to a sharp point, to easily penetrate surrounding tissue.

As apparent from FIGS. 9 and 9A upward and lateral motion of tips 18 of elongated strand 12 is complete once tips 18 are proximate with central portion 14.

Tips 18 may penetrate exterior surface tissue 13 of a vessel 11 without passing entirely through the tissue of vessel 11. Alternatively, tips 18 may penetrate entirely through vessel 11 or other tissue in which an aperture is to be closed with the tips extending out of the exterior of the vessel or other tissue in which an aperture is to be closed. As yet another alternative, tips 18 may be dull and serve only to press against the surface of tissue surrounding an aperture to be closed, with 18 tips serving to draw the tissue together without penetration of the tissue by tips 18. The clip may be provided with tips 18 sharpened or dull depending upon the clinical used for the particular clip of interest.

Referring again to FIGS. 9 and 9A, when clip 10-1 is fully deployed, upper horizontally extending side arms 30 preferably remain substantially outboard of the aperture of the vessel, the undersides 31 of horizontally extending side arms 30 preferably are in contact with the vessel tissue.

Figure 15:
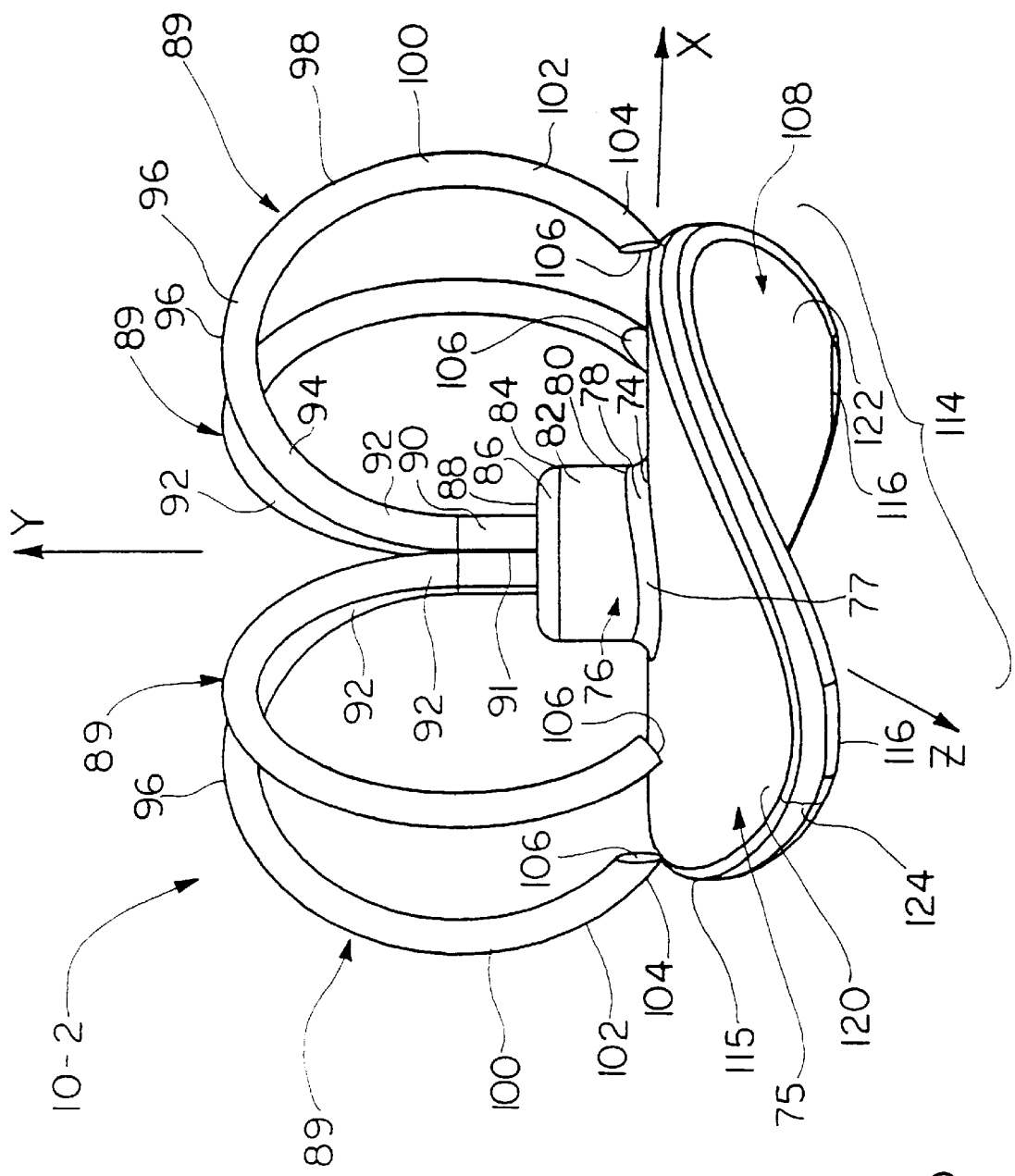
FIG. 15 is a front quarter view of a second embodiment of a tissue closure clip in accordance with the invention.

Referring to FIGS. 15 through 20 in another aspect of the invention a closure clip has a saddle configuration wherein elongated strand portions 89 extend from a stem 76 supported by a saddle shaped bottom piece 108. Considering for purposes of reference a three dimensional coordinate system having axes X, Y and Z as illustrated in FIG. 15, a midpoint of stem 76 defines the origin of the X, Y, Z coordinate system. Coincident with the Y axis is a position from which four curving extremity portions 89 extend first in a generally upwardly direction along the Y axis and transition to gradually curving in an outwardly direction. Saddle portion 75 extends three dimensionally in the X-Z plane and curves downwardly in the Y-Z and X-Y planes.

Still referring to FIGS. 15 through 20, stem 76 includes sections 78, 82 and 86. Base portion 78 transitions to an exterior upper surface 120 of downwardly curved saddle portion 75 providing juncture between saddle 75 and stem 76. Surface 77 of base portion 78 curves outwardly to tangentially join exterior surface 120 of downwardly curved saddle portion 75.

An upper end of base portion 78 transitions to mid-stem support piece 82 through juncture 80. Mid-stem support piece 82 transitions to top stem closure piece 86 through juncture 84. Stem 76 is the anchor for extending portions 89. Generally, each of four curved extending portions 89 extend in a linear upwardly direction out of piece 90 and are coincident with each other at a position of tangency 91.

Areas of transition 94 define transition from upwardly and outwardly curved portions 92 to peak central portions 96 wherein peak central portions 96 define the parts of curved extending portions farthest from exterior surface of curved saddle portion 75. Peak central portions 96 transition into outwardly and downwardly curved portions 98 which in turn transition to outwardly curved portions 100 defining the portion farthest from piece 90. Outwardly curved portions 100 transition into inwardly curved portions 102 thereby transitioning to front end portions 104 terminating in tips 106. Preferably tips 106 comprise a sharp point to pierce tissue surrounding the aperture to be closed. Exterior surface 120 of saddle 75 meets juncture segment 74 defining commencement of stem 76.

Saddle portion 75 has a circular periphery and a configuration in which two opposing sides curve downwardly with transition portions 116 being lower than transition portions 118.

Preferably, to form the saddle configuration the sides of saddle portion 75 curve downwardly to transition portions 116, continue therethrough to upwardly curved portions 115 and then to transition portions 118.

Figure 16:
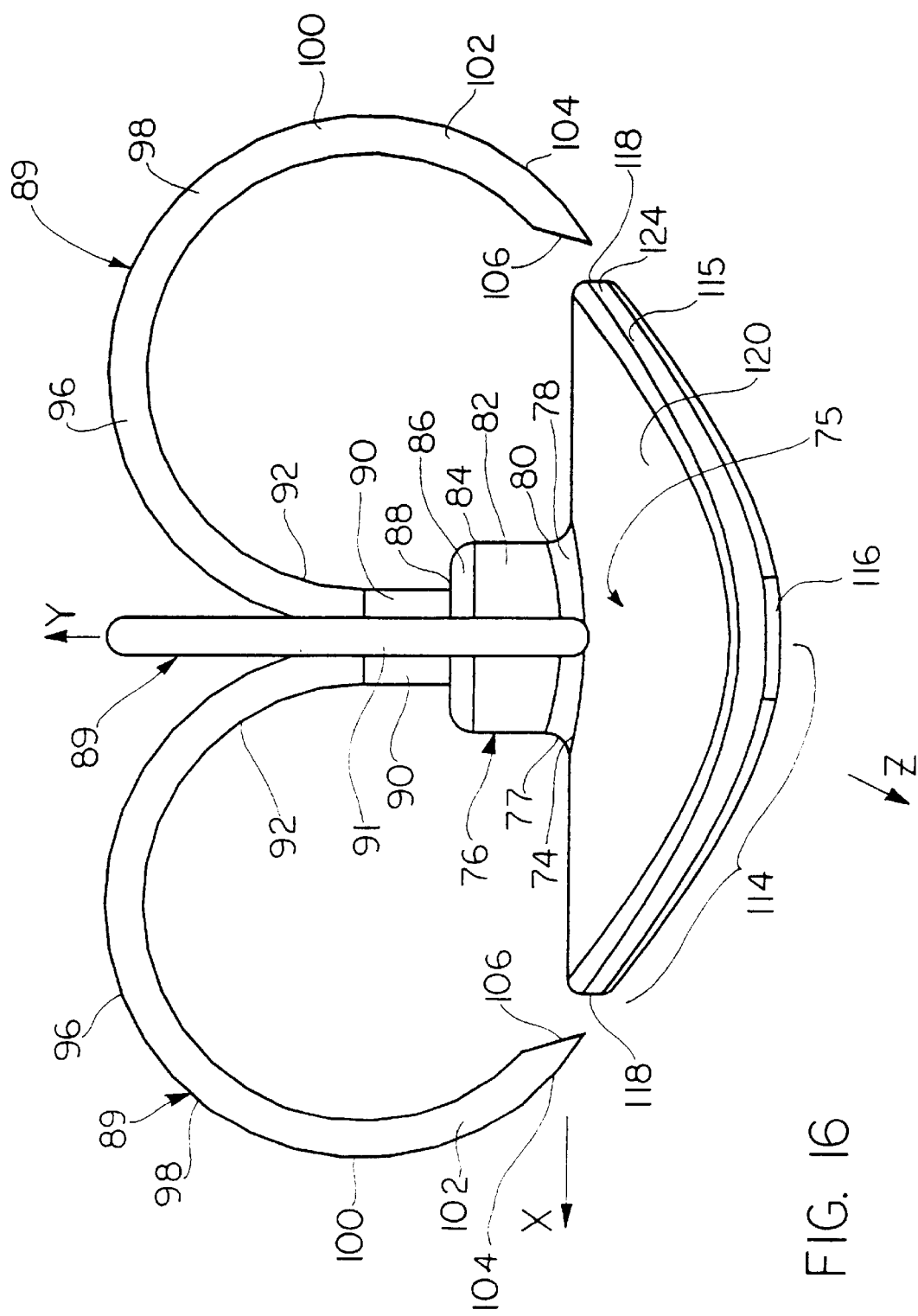
FIG. 16 is a side view of the clip illustrated in FIG. 15.
Figure 17:
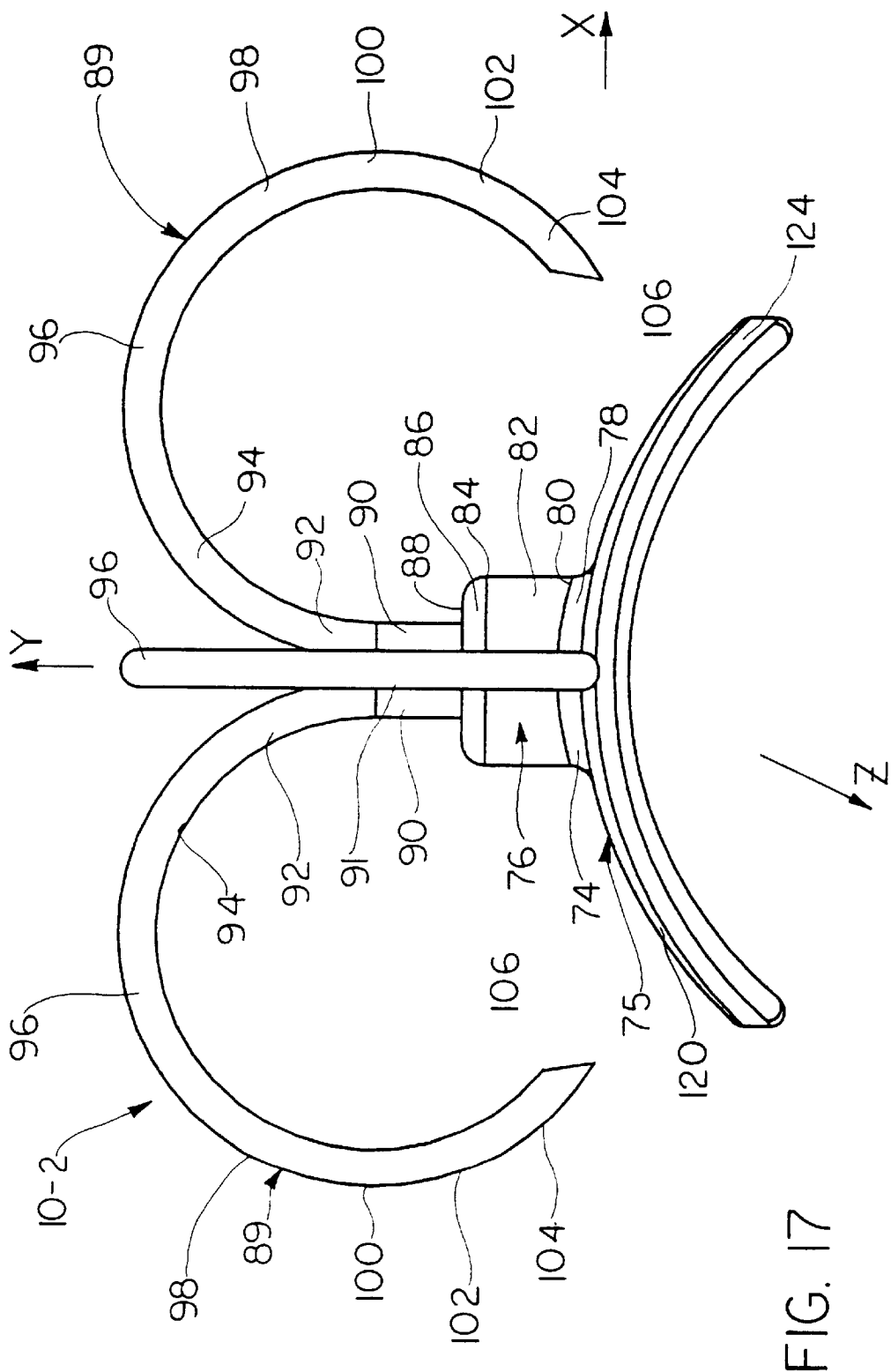
FIG. 17 is a front view of the clip illustrated in FIGS. 15 and 16.

Referring to FIG. 16, curved extending portions 89 when relaxed extend outwardly towards the four transition portions 116, 118, 116 and 118 respectively.

In FIG. 16 the downward curvature of saddle 75 is depicted. Tips 106 of portions 89 are proximate with but separated from transition portions 116 and 118.

Referring to FIGS. 15 through 20, sides 124 of saddle configuration bottom piece are preferably curved. Curvature of sides 124 prevents abrasion within the vessel and minimizes discomfort to the patient.

Figure 18:
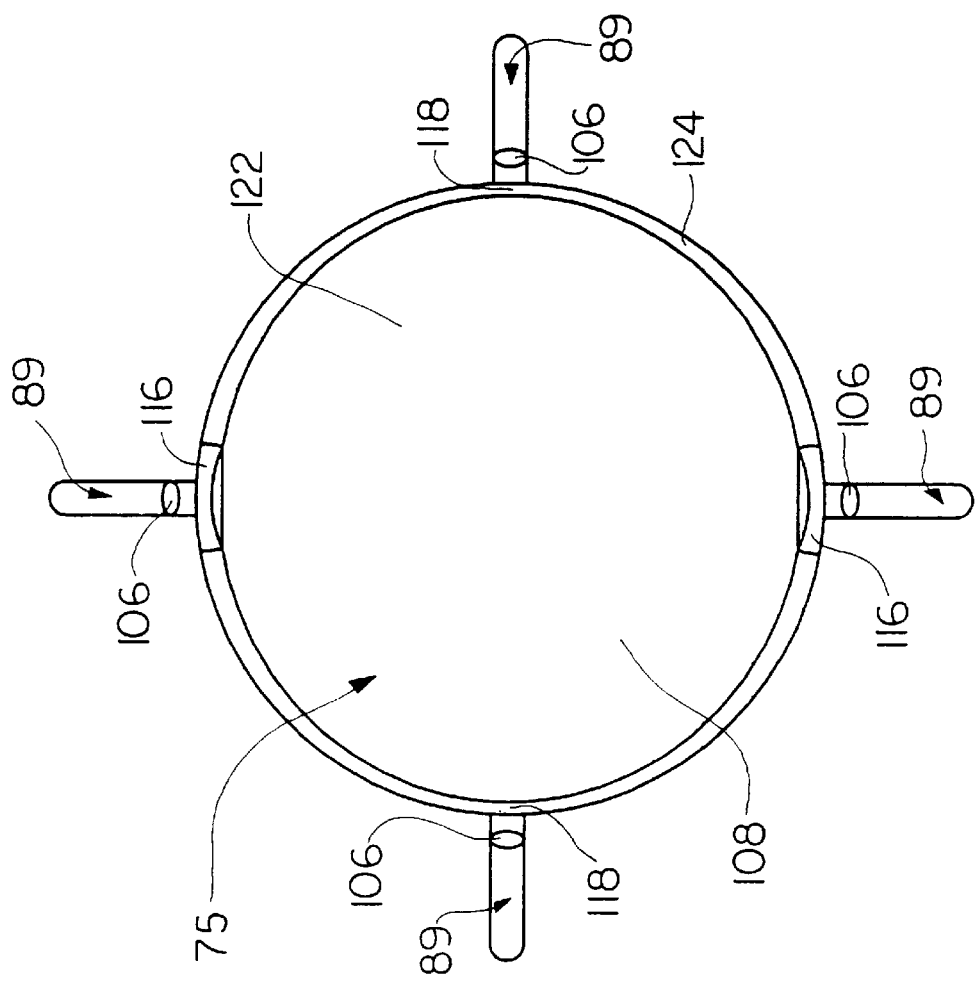
FIG. 18 is a bottom view of the clip illustrated in FIGS. 15, 16 and 17.
Figure 19:
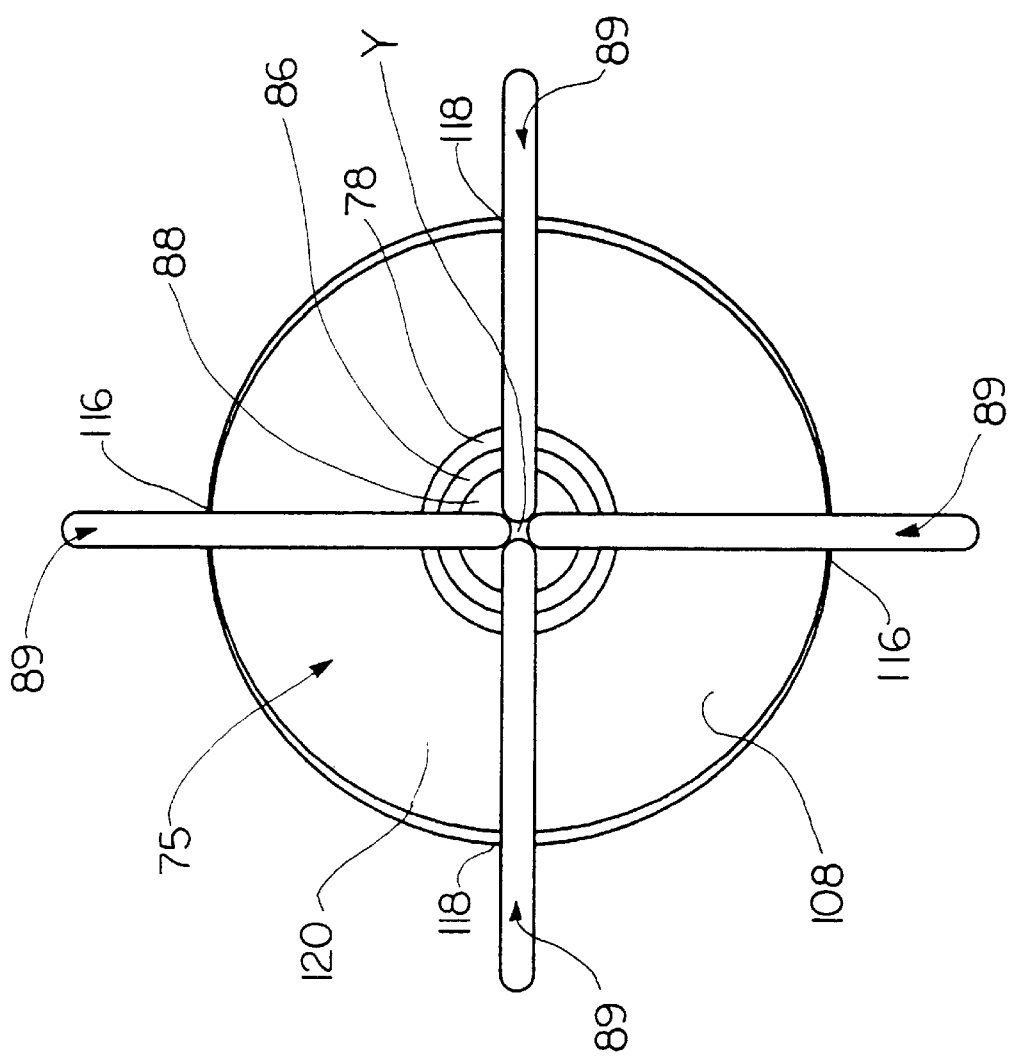
FIG. 19 is a top view of the clip illustrated in FIGS. 15, 16, 17 and 18.

FIGS. 18 and 19 illustrate that bottom surface 122 transitions to curved edges 124. Rotation of saddle configured bottom piece 108 about the X axis by 180° is depicted in FIG. 19 wherein portions 89 extend beyond circumferential curved edge 124 of saddle 75.

Referring to FIGS. 20 and 21, a third embodiment of a tissue closure clip manifesting aspects of the invention is designated generally 10-3 and preferably includes a plurality of elongated strands, where the individual strands are designated generally 12-3 in FIGS. 20 and 21. Strands 12-3 may be single filaments or may be woven or braided or other arrangements of multiple sinuous members. Each elongated strand 12-3 preferably has a central portion and two (2) extremity portions extending in either direction from the central portion. Individual central portions of the elongated strands 12-3 are designated 14-3 while extremity portions of each elongated strand 12-3 are designated 16-3. Each extremity portion 16-3 terminates in a tip, where the tips of individual extremity portions are individually designated 18-3. Each tip 18-3 of an extremity portion 16-3 is shaped to retain tissue about the periphery of an aperture, which tissue is encountered by a tip 18-3 of tissue closure clip 10-3 as clip 10-3 deploys upon release from or by a delivery member. A portion of one suitable delivery member is illustrated in FIG. 22; the illustrated portion is designated generally 20 therein.

As apparent from FIG. 21 a plurality of elongated strands 12-3, preferably comprised of memory metal, originate from a central region 19-3 wherein elongated strands 12-3 and a longitudinally extending loading wire 210 are retained within a central band 21-3.

Elongated strands 12-3 preferably extend upwardly and downwardly from central region 19-3; band 21-3 retains central portion 14-3 of elongated strands 12-3. Elongated strands 12-3 curve outwardly from central portion 14-3.

A longitudinally extending load wire loop 210 preferably extends from within central region 19-3 and is constrained by band 21-3. Loading wire 54 loops through loop 210 to draw medical clip 10-3 into ejection chamber 56-3.

Referring to FIG. 22, front end 52-3 of clip delivery member 20-3 is depicted in the course of ejecting clip 10-3 from ejection chamber 56 wherein elongated strands 12-3 are in a linear, constrained configuration. Upon ejection, elongated strands 12-3 curve outwardly from central region 19-3, contacting and preferably piercing tissue above and below the center of the clip. Clip 10-3 differs from clips 10-2 and 10-1 in providing bilateral aperture closure, above and below the clip center, inside and outside of the vessel of interest.

Referring now to FIG. 11, a preferred embodiment of a clip delivery member according to one aspect of the invention is designated generally 20 and functions to eject a clip 10, preferably the preferred embodiment of clip 10-1, to close a vessel aperture. In one embodiment clip delivery member 20 comprises a longitudinally extending housing 40 receivably housing a push rod 44 which is manually activated by pushing a "firing" button 48 wherein firing button 48 is separable from an associated pull ring 46. Push rod 44 is basically contacted by firing button 48 with the end of push rod 44 opposite from that contacted by firing button 48 contacting an upper end of a clip 10 to force the clip out of tube 55 in a two stage ratchet-like action as described above.

Preferably, side arms 50 extend outwardly, perpendicular to longitudinally extending chamber 38, facilitating manual "firing" of clip 10 and manual aim of clip delivery member 20. Side arms 50 may be grasped by an operator, using the fingers while the thumb may be used to "fire" push rod 44 with firing button 48.

Referring to FIG. 11, within front end 52 is a hollow chamber 56 of adequate sizes to receive clip 10-1. Top portion of clip 10-1 contacts distal end 69 of push rod 44 where push rod 44 linearly extends within longitudinally extending chamber 56. A proximal end 68 of push rod 44 facingly contacts cylindrical firing button 48 which in turn is connected to, yet detachable from, a pull ring 46.

An expanded view of an optionally configured front end 52 of clip delivery member 20 illustrated in FIG. 10 shows front end 52 having a hollow tubular opening 53 with two grooves 58 are angularly positioned 180° apart. As wire 54 connected to ring 46 in FIG. 11 is drawn by pulling ring 46, clip 10-1 is drawn into front end 52 by having first portion 200 distend upwardly in the direction of vertical axis A illustrated in FIGS. 1 and 2 so that third portions 206 extend the farthest radially outwardly of any portion of clip 10-1. Referring to FIG. 11, clip 10-1 is drawn into front end 52 by loading wire 54 wherein loading wire 54 loops through crossover juncture 36 of closure clip 10-1 and attaches to pull ring 46.

Push rod 44 ejects clip 10-1 by urging the upper portion 64 of clip 10-1 downwardly out of ejection chamber 56.

Clip 10-1 facilitates rapid closure of a tissue aperture. Preferably, clip 10-1 is constructed of memory metal and when unconstrained assumes the configuration illustrated in FIGS. 1 through 6. The memory metal construction of clip 10-1 allows clip 10-1 to be constrained in an elongated conformation, for example when within ejection apparatus 20 depicted in FIG. 6. Upon ejection, clip 10-1 preferably pierces proximate tissue and pulls the tissue together when clip 10-1 coils to its unconstrained configuration.

In another aspect of the invention an optional front end 52 of a preferred embodiment of clip delivery member 12 is depicted in FIGS. 23 through 27. In this aspect of the invention tube 55 contains two longitudinally extending side chambers 128 angularly positioned equidistant from each other.

Side chambers 128 contain strips 130 of memory metal that may extend through apertures 126 located on opposite sides of tube 55 equidistant from each other within front end 52 of clip delivery member 12.

Referring to FIGS. 23 through 25, extension of memory metal strip 130 through aperture 126 results in formation of a loop 140 proximate the front end 52 of clip delivery member 12.

Figure 26:
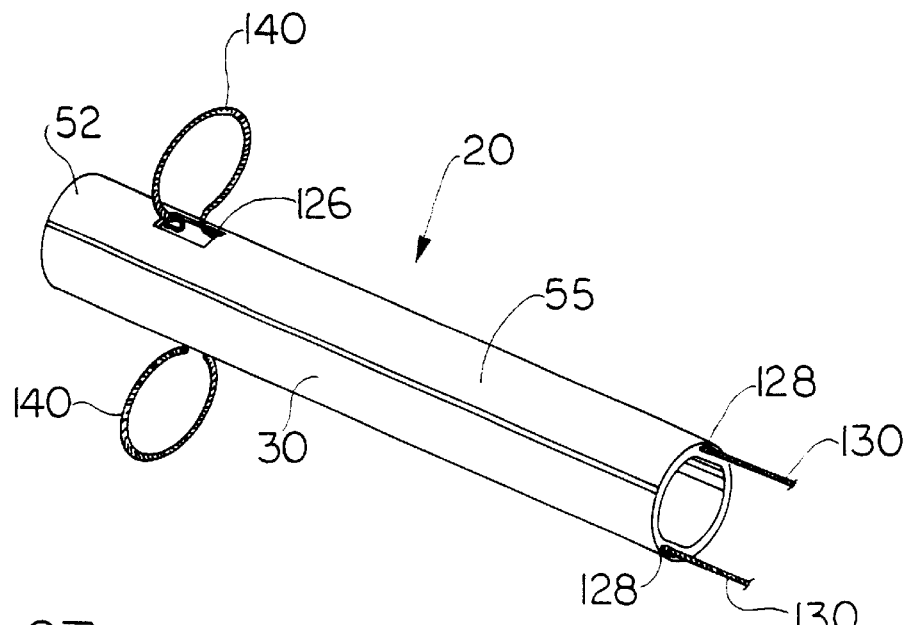
FIG. 26 is an isometric view of a portion of a clip delivery member of the type generally illustrated in FIGS. 23 through 25 showing a clip delivery positioning loop extending from the exterior of the clip delivery member.
Figure 27:
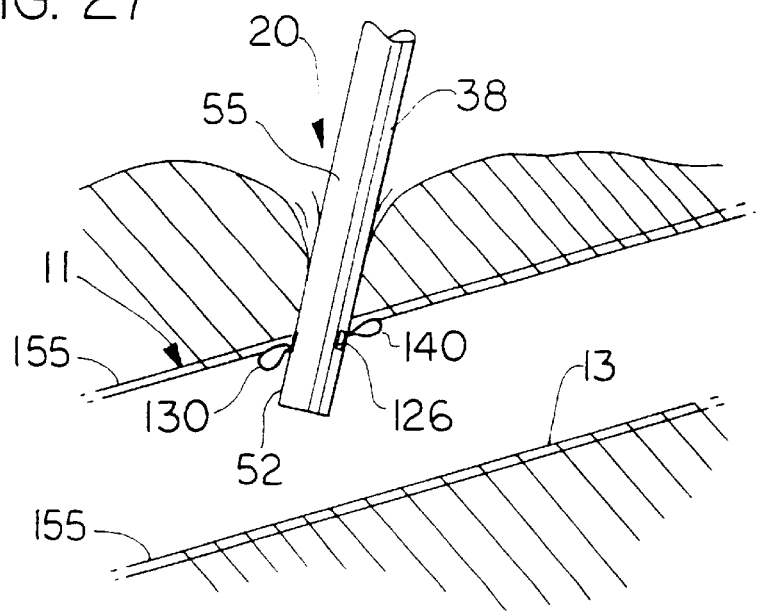
FIG. 27 is a broken, partially sectioned side view of the clip delivery member illustrated in FIG. 26 in place within tissue ready to eject a clip into place to close an aperture.

Referring to FIGS. 26 and 27 dual side loops 140 act to position clip 10 properly within a vessel. FIG. 27 illustrates positioning of clip delivery member 12 within a vessel.

In FIGS. 24 and 25 only one longitudinally extending side chamber 128 is contained within tube 55 wherein loop 140 is formed through one aperture 126. Referring to FIG. 23, positioning within the vessel is accomplished by one loop 140 rather than two.

Ejection of clip 10 may be accomplished with or without loops 140.

In operation, medical clip 10 returns to the unconstrained configuration rapidly to seal the aperture with minimal discomfort to the patient.

Figure 28:
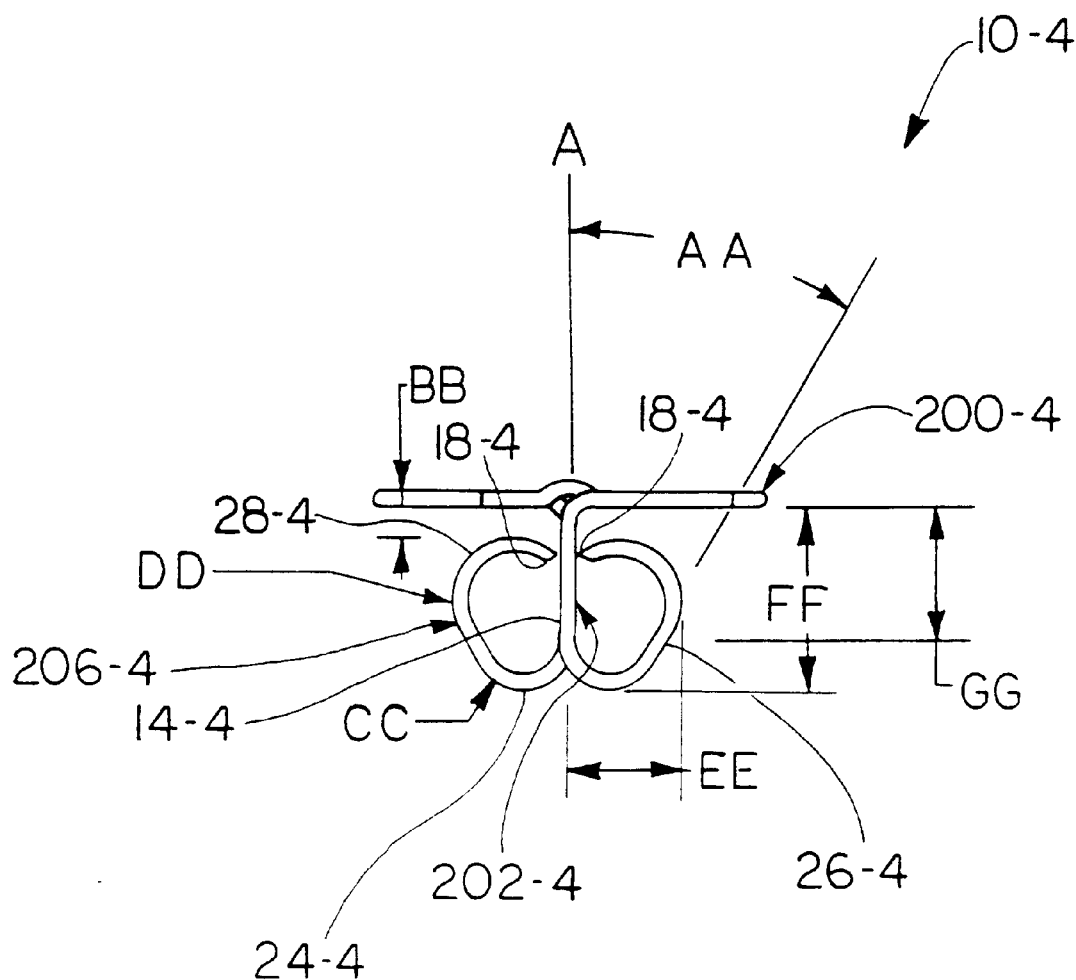
FIG. 28 is a front view of a fourth embodiment of a clip in accordance with the invention where the clip illustrated in FIG. 28 is similar to the embodiment illustrated in FIGS. 1 through 6, 13 and 14, the difference being that the embodiment of the clip illustrated in FIG. 28 has a planar upper portion.
Figure 30:
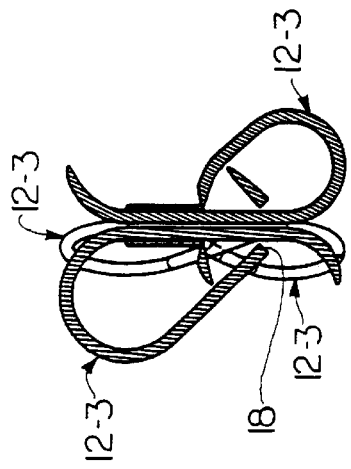
FIG. 30 is a sectional view of the clip illustrated in FIG. 29 taken at lines and arrows 30—30 in FIG. 29.
Figure 32:
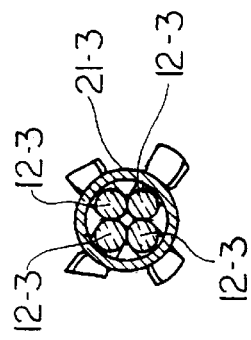
Figure 29:
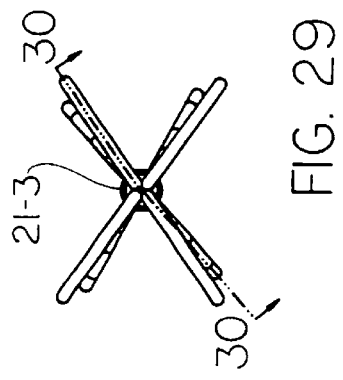
FIG. 29 is a top view of the embodiment of the clip illustrated in FIG. 21 fabricated without loading loop 210 illustrated in FIG. 21.
Figure 31:
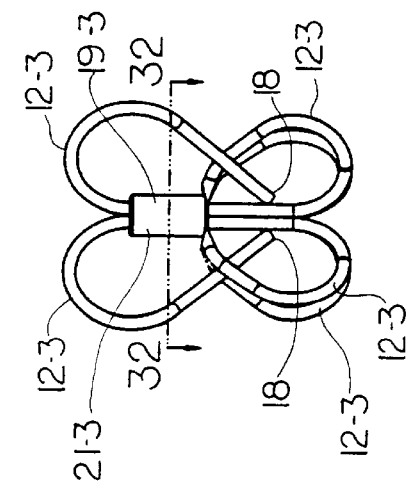
FIG. 31 is a front view of the clip illustrated in FIG. 29.
Figure 33:
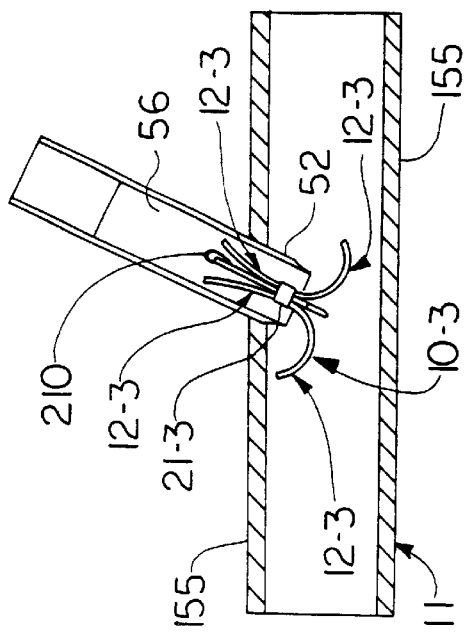
FIG. 33 is a broken vertical section illustrating deployment of a clip in accordance with the third embodiment of the invention to close an aperture and a vessel wall with the clip undeployed and fully within the clip delivery apparatus.
Figure 34:
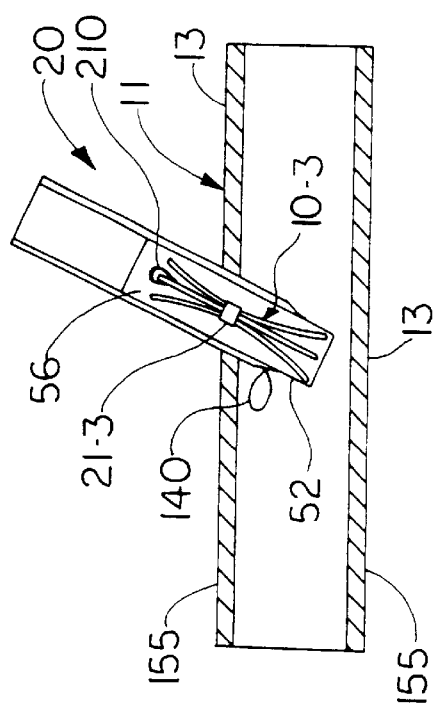
FIG. 34 is a broken vertical section similar to FIG. 33 but with the clip 10-4 partially ejected from the delivery apparatus and in the first stage of deployment.
Figure 35:
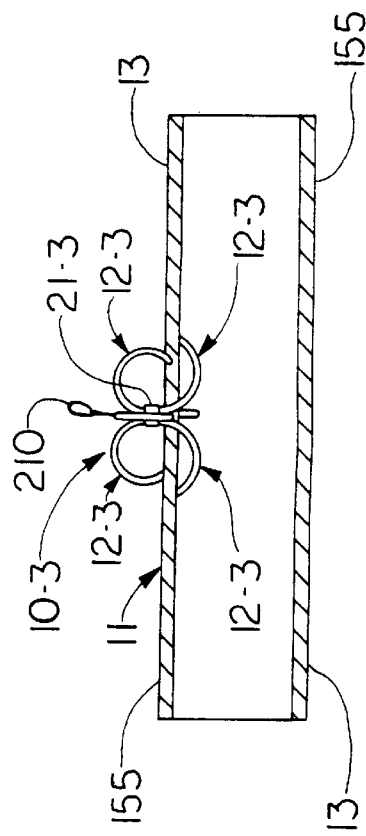
FIG. 35 is a partially broken vertical section similar to FIGS. 33 and 34 depicting clip 10-3 fully deployed in a vessel of interest, closing an aperture within the vessel by action of extremity portions 12-3 penetrating the vessel wall on both the inside and the outside of the vessel and drawing the vessel wall radially and leaving thereby to close the aperture of interest.

Referring to FIG. 28 illustrating a fourth embodiment of a clip manifesting the invention where the clip is designated generally 10-4, clip 10-4 is preferably fabricated with an angle between vertical axis A and a line parallel with upwardly extending central segment 26-4 of third portion 204 equal to about thirty degrees (30°) where this angle is indicated by indicator AA in FIG. 28. Clip 10-4 is fabricated preferably with space between first portion 200-4 and the vertically upper extremity of third portion 206-4, designated by dimensional indicator BB in FIG. 28, being about 0.037 inches.

Clip 10-4 is further preferably fabricated with the radii of the arcs defining transition portion 24-4 between second portion 202-4 and forming the transition thereof into third portion 206-4 is formed preferably having a radius of about 0.048 inches as indicated by arrow CC in FIG. 28 and with transition 284 between the central part of third portion 206 and tip 18-4 being formed on a radius of about 0.063 inches as indicated by DD in FIG. 28.

Clip 10-4 illustrated in FIG. 28 is further preferably fabricated having a distance of about 0.119 inches between vertical axis A and the redial outer extremity of third portion 206 as indicated by dimensional indicator EE in FIG. 28.

Clip 10-4 is further preferably fabricated such that clip 10-4 has an overall height of about 0.206 inches as indicated by dimensional indicator FF in FIG. 28. Clip 10-4 is further preferably fabricated having a distance from the underlying surface of first portion 200 to a locale of transition between central portion 14 and third portion 206 as indicated by dimensional indicator GG in FIG. 28 of about 0.150 inches.

While the invention has been described with respect to closing apertures and vessels, the invention is not limited to this. Specifically, the invention has applicability to closing laparoscopic portals, to pistula which are leaks in the bowel to closing holes in the heart to dealing with froamen ovals, congenital holes, ventricular central defects, arterial central defects and other apertures in the aorta and associated pulmonary arteries and veins.

What is claimed is:

1. Clip apparatus for closing a vessel aperture resulting from insertion of a surgical implement comprising:
    a. an elongated strand comprising a central portion and extremity portions extending from said central portion, the extremity portions having tips;
    b. the tips of said extremity portions remote from said central portion being shaped to retain tissue encountered thereby;
    c. said extremity portions having memory characteristics seeking to cause said extremity portions to curl with respect to said central portions to retain tissue engaged thereby when said strand is in an unconstrained disposition; and
    d. an elongated member extending radially outwardly with respect to the central portion, the elongated member having an elongated vessel engaging surface dimensioned to block blood flow.

2. Clip apparatus of claim 1, wherein said strand further comprises:
    a. a pair of mid-portions intermediate said tips and said central portion; and wherein
    b. said central portion is disposed in a first plane; and
    c. said mid-portions are disposed in a plane transverse to said first plane.

3. Clip apparatus of claim 1, wherein the extremity portions reside on an exterior surface of the vessel.

4. Clip apparatus of claim 1, wherein when loaded in a device for deployment, the clip apparatus is in an extended configuration.

5. Clip apparatus of claim 1, wherein the tips of the extremity portion penetrate the vessel.

6. Clip apparatus for closing a vascular aperture resulting from insertion of a surgical implement thereinto subsequent to completion of an invasive therapeutic procedure and withdrawal of said implement, comprising:
    a. a plurality of elongated strands each comprising a central portion and extremity portions extending from said central portion, the extremity portions having tips;
    b. the tips of said extremity portions remote from said central portion being shaped to retain tissue encountered thereby;
    c. said extremity portions having memory characteristics seeking to cause said extremity portions to curl with respect to said central portion when said strands are in an unconstrained disposition; and
    d. an elongated saddle-shaped bottom piece having an elongated vessel engaging surface dimensioned to block blood flow.

7. Clip apparatus of claim 6, wherein sides of the bottom piece are curved.

8. Clip apparatus of claim 6, wherein the elongated strands are formed from a one piece integral strand.

9. Clip apparatus of claim 6, wherein cross sections of said strands are circular.

10. Apparatus for closing a vascular aperture comprising a clip having an upper half and a lower half, the upper half having a plurality of extremity portions extending from a central portion and curving outwardly with respect to the central portion when released from a delivery member to engage tissue, the extremity portions being composed of shape memory material, the lower half having an elongated member extending radially outwardly with respect to the central portion and having a vessel engaging surface to block blood flow.

11. Clip apparatus of claim 10, wherein the extremity portions pierce tissue.

12. Clip apparatus of claim 10, wherein the elongated member has a curved configuration.

13. A method for closing a lumen aperture resulting from insertion of a surgical implement thereinto subsequent to completion of an invasive therapeutic procedure and withdrawal of said implement from said aperture, comprising:
    a. providing an elongated strand comprising a central portion and extremity portions extending from said central portion, tips of said extremity portions remote from said central portion being shaped to retain lumen encountered thereby and said extremity portions having memory characteristics seeking to cause said extremity portions to curl towards one another and over one another about said central portions when said strand is in an unconstrained disposition, free of externally applied stress;

b. dispensing said elongated strand from a tubular housing partially into said lumen aperture sufficiently for a dispensed portion consisting of a strand section from a strand extremity to said central portion to curl about and towards said central portion thereby encountering lumen about the periphery of said aperture and drawing said aperture periphery radially inwardly relative to a longitudinal axis of said strand; and c. dispensing a remaining portion of said strand from said housing thereby permitting said remaining portion of said strand from said central portion to a second strand extremity to curl about and towards said central portion thereby encountering lumen about the periphery of said aperture on the exterior of said lumen and drawing said aperture periphery radially inwardly relative to a longitudinal axis of said strand thereby to substantially close said lumen.

* * * * *